United States Patent [19]

Skulnick et al.

[11] Patent Number: 4,477,442
[45] Date of Patent: Oct. 16, 1984

[54] COMPOSITION OF MATTER AND PROCESS

[75] Inventors: Harvey I. Skulnick, Oshtemo; Harold E. Renis, Portage, both of Mich.

[73] Assignee: The Upjohn Company, Kalamazoo, Mich.

[21] Appl. No.: 206,311

[22] Filed: Nov. 5, 1980

Related U.S. Application Data

[63] Continuation of Ser. No. 66,251, Aug. 9, 1979, abandoned, which is a continuation of Ser. No. 968,876, Dec. 12, 1978, Pat. No. 4,239,753, which is a continuation of Ser. No. 802,504, Jun. 1, 1977, abandoned, which is a continuation-in-part of Ser. No. 715,663, Aug. 19, 1976, abandoned.

[51] Int. Cl.³ .................... A61K 31/70; A61K 31/71
[52] U.S. Cl. ..................................... 424/180; 424/181
[58] Field of Search ................................ 424/180, 181

[56] References Cited

U.S. PATENT DOCUMENTS

| | | | |
|---|---|---|---|
| 3,907,779 | 9/1975 | Deboer et al. | 424/181 |
| 4,022,889 | 5/1977 | Bannister et al. | 424/181 |
| 4,171,431 | 10/1979 | Skulnick | 424/180 |

Primary Examiner—Jerome D. Goldberg
Attorney, Agent, or Firm—William G. Jameson

[57] ABSTRACT

A process for treating viral diseases in humans and animals which comprises administering a therapeutic amount of a compound of the formula

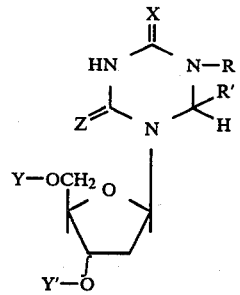

the compounds are formulated with pharmaceutical carriers for systemic or local means of administration.

18 Claims, 1 Drawing Figure

TABLE 1
| | | MST | %S |
|---|---|---|---|
| ● SALINE | | 6.3 | 5 |
| ○ U44590 | 400 mg./kg. | 20.8 | 85 |
| □ U44590 | 200 | 16.8 | 60 |
| △ U44590 | 100 | 14.2 | 45 |
| ▽ U44590 | 50 | 12.8 | 40 |
| ■ U50365 | 200 | 17.4 | 70 |
| ▲ U50365 | 100 | 14.2 | 45 |
| ▼ U50365 | 50 | 7.4 | 10 |
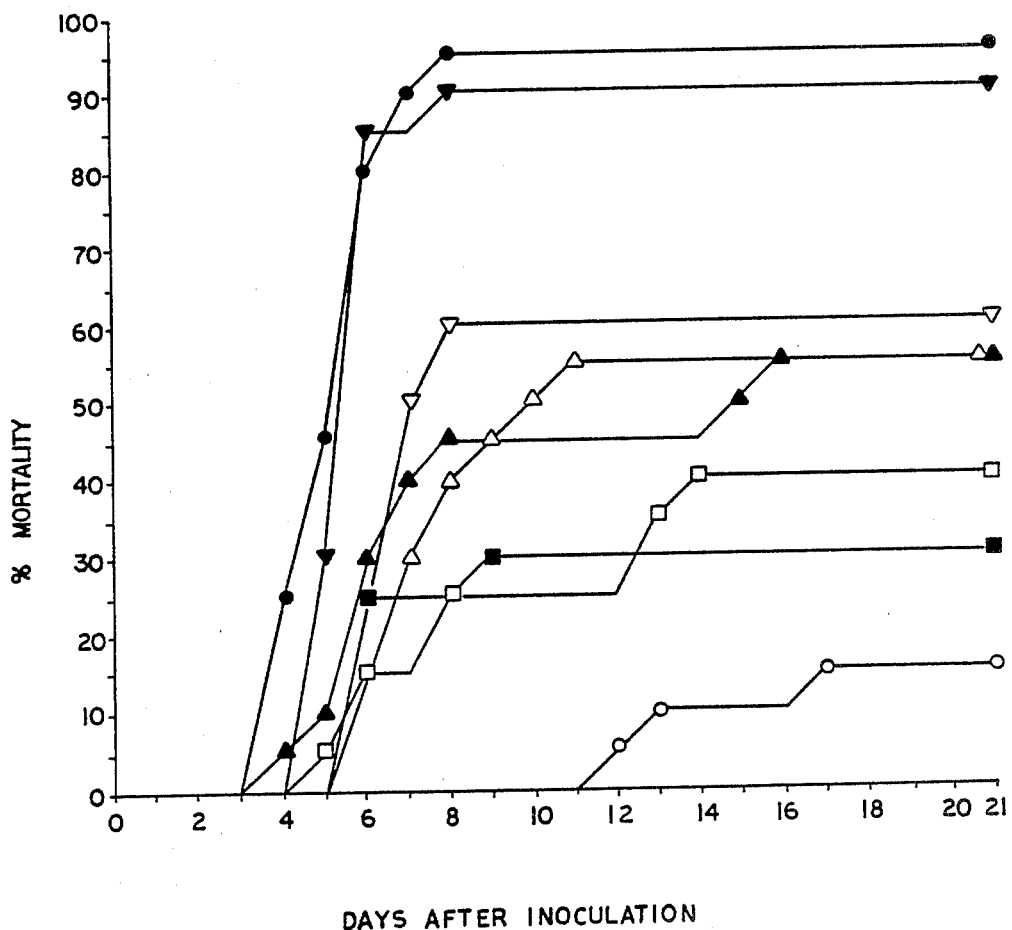
DAYS AFTER INOCULATION

COMPOSITION OF MATTER AND PROCESS

CROSS REFERENCE TO RELATED APPLICATION

This is a continuation of application Ser. No. 066,251, filed Aug. 9, 1979, now abandoned, which is a continuation of application Ser. No. 968,876, filed Dec. 12, 1978, now U.S. Pat. No. 4,239,753 (issued Dec. 16, 1980), which is a continuation of application Ser. No. 802,504, filed June 1, 1977, now abandoned, which is a continuation-in-part of application Ser. No. 715,663, filed Aug. 19, 1976, which is now abandoned.

BACKGROUND OF THE INVENTION

U.S. Pat. No. 3,907,779 issued Sep. 23, 1975 describes and claims the compound 1-(2-deoxy-β-D-ribofuranosyl)-5-methyl-5,6-dihydro-s-triazine-2,4-(1H,3H)-dione and various derivatives thereof.

U.S. Pat. No. 3,907,779 describes the original discovery, identification and production of 1-(2-deoxy-β-D-ribofuranosyl)-5-methyl-5,6-dihydro-s-triazine-2,4-(1H,3H)-dione by the controlled fermentation of the microorganism Streptomyces platensis var. clarensis, NRRL 8035. U.S. Pat. No. 3,907,779 does not describe the production of the present compounds and it is not clear how this objective might be accomplished with the microorganism.

SUMMARY OF THE INVENTION

Disclosed are pharmaceutical compositions of organic chemical compounds which can be used to treat viral diseases in humans and animals. The invention is more particularly directed to novel anti-viral 1-(2-deoxy-β-D-pentofuranosyl)-5,6-dihydro-s-triazines and derivatives thereof.

The 1-(2-deoxy-β-D-pentofuranosyl)-5,6-dihydro-s-triazines and derivatives thereof are active against various DNA viruses, for example, the Herpes virus Type 1 and thus, can be used to control such virus where its presence is not desired.

DETAILED DESCRIPTION OF THE INVENTION

In accordance with this invention, the 1-(2-deoxy-β-D-pentofuranosyl)-5,6-dihydro-triazines are represented by structure Ia.

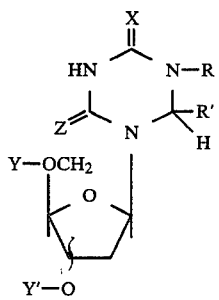

wherein it is understood that Ia can exist in tautomeric forms, for example, Ib and Ic and that the compounds of this invention are likely to be mixtures of all tautomeric forms, the percentages of each tautomer to be at least partially dependent on the nature of X, R, R', Z, Y and Y', and the physical environment of the compound.

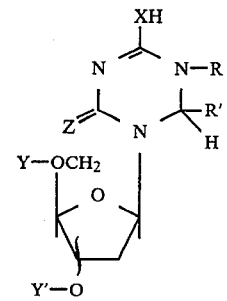

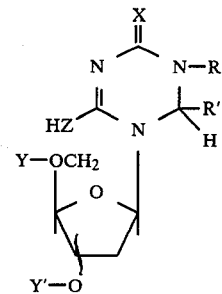

For the purpose of brevity throughout the application and claims, the compounds will be referred to hereinafter in their tautomeric form, corresponding to structure Ia.

The X substituent is selected from the group consisting of oxygen, imino, lower-alkylimino, and lower-acylimino; R' is selected from the group consisting of hydrogen and loweralkyl; Y is selected from the group consisting of hydrogen, carboxacyl of from 1 through 18 carbon atoms, and phosphono; Y' is selected from the group consisting of carboxacyl and hydrogen; Z is selected from the group consisting of oxygen and sulfur; R is selected from the group consisting of hydrogen, methyl, ethyl, n-propyl, isopropyl, phenyl, benzyl, cyclopropyl, lower-alkoxylower-alkyl, and lower-alkylthiolower-alkyl with the proviso that when R' is hydrogen X and Z are oxygen, Y is hydrogen, carboxacyl of from 1 through 18 carbon atoms or phosphono, and Y'—O is in the erythro position, then R is hydrogen, ethyl, n-propyl, isopropyl, phenyl, benzyl, cyclopropyl, lower-alkoxy, lower-alkyl, or lower-alkylthiolower-alkyl; and pharmaceutically acceptable salts thereof when X is imino or lower-alkylimino or when Y is phosphono.

The wavy line joining Y'—O to the body of the molecule as shown in formula Ia indicates that the Y'—O may be in either the erythro or threo configuration.

The term "carboxacyl" as used through the specification and claims means the acyl radical of a hydrocarbon carboxylic acid having from 1 to about 18 carbon atoms, inclusive, or of a hydrocarbon carboxylic acid substituted with an inert group. Representative of such carboxacyl groups are those of the formula:

wherein E is hydrocarbyl of from 1 to about 17 carbon atoms, inclusive or hydrocarbyl of from 1 to about 17 carbon atoms, inclusive, wherein a hydrogen atom has been replaced with an inert substituent group. Illustrative of acyl radicals of a hydrocarbon carboxylic acid wherein E is hydrocarbyl are the acyl radicals of (a) saturated or unsaturated, straight or branched chain aliphatic ccarboxylic acids, for example, acetic, propionic, butyric, isobutyric, tert-butylacetic, valeric, isovaleric, caproic, caprylic, decanoic dodecanoic, lauric, tridecanoic, myristic, pentadecanoic, palmitic, margaric, stearic, acrylic, crotonic undecylenic, oleic, hexynoic, heptynoic, octynoic acids and the like; (b) saturated or unsaturated, alicyclic carboxylic acids, for example, cyclobutanecarboxylic acid, cylopentanecarboxylic acid, cyclopentenecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropionic acid, and naphthylacetic acid, and the like.

The term "hydrocarbon carboxylic acid substituted with an inert group" is used herein to mean a hydrocarbon carboxylic acid wherein one or more hydrogen atoms attached directly to a carbon atom have been replaced with a group inert to reaction under the conditions hereinafter described for preparing compounds (I) of the invention. Illustrative of such substituent groups are halo-, nitro-, hydroxy-, carboxy-, amino-, cyano-, thiocyano-, or alkoxy-groups. Illustrative of halo-, nitro-, hydroxy-, carboxy-, amino-, cyano-, thiocyano- and alkoxy- substituted hydrocarbon carboxylic acids are mono-, di, and trichloracetic acid; α- and β- chloropropionic acid; α-and β-bromobutyric acid; α-and δ iodovaleric acid; mevalonic acid; 2- and 4-chlorocyclohexanecarboxylic acid; shikimic acid; 2-nitro-1-methylcyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo 2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylicyclohexanecar-acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentisic acid; o-, m-, and p-chlorobenzoic acid; anisic acid; salicyclic acid; p-hydroxybenzoic acid; β-resorcylic acid; gallic acid; veratric acid; trimethoxybenzoic acid; trimethoxycinnamic acid; 4,4'-dichlorobenzillic acid; 0-, m-, and p-nitrobenzoic acid; cyanoacetic acid; 3,4-and 3,5-dinitrobenzoic acids; 2,4,6-trinitrobenzoic acid; thiocyanoacetic acid; cyanopropionic acid; latic acid; ethoxyformic acid (ethyl hydrogen carbonate); butyloxyformic acid; pentyl oxyformic acid hexyloxyformic acid; dodecyloxyformic acid; hexadecyloxyformic acid; malonic acid; succinic acid; glutaric acid and the like.

The term "lower alkyl" is employed in its ususal sense as meaning alkyl of from 1 to 4 carbon atoms, inclusive, such as methyl, ethyl, propyl, butyl and isomeric forms thereof.

The term "lower-alkoxylower-alkyl" as used throughout the specification and claims means lower alkyl of from 1 to 4 carbon atoms, inclusive, substituted by alkoxy of 1 to 4 carbon atoms, inclusive. Illustrative of lower-alkoxylower-alkyl are methoxymethyl, ethoxymethyl, propoxymethyl, 2-ethoxyethyl, 1-ethoxyethyl and the like.

The term "lower-alkylthiolower-alkyl" as used throughout the specification and claims means lower-alkyl of from 1 to 4 carbon atoms, inclusive, substituted by alkylthio of from 1 to 4 carbon atoms.

Illustrative of lower-alkylthiolower-alkyl are methylthiomethyl, ethylthiomethyl, propylthiomethyl, 2-methylthioethyl, 1-methylthioethyl, 2-ethylthioethyl, 4-methylthiobutyl and the like.

The term "loweracylimino" as used herein means an imine function substituted by an acyl radical of form 1 to 4 carbon atoms, inclusive.

Illustrative of loweracylimino are acetylimino, n-butyroylimino and the like.

The term "pharmaceutically acceptable salts" as used throughout the specification and claims means all pharmaceutically acceptable salts of the compounds, including, for example, acid addition salts of compounds of formula Ia such as hydrochloride, sulfate acetate and the like. When X is imino or lower-alkylimino; as well as salts derived from the phosphate function when Y is phosphono, such as sodium, potassium, calcium and ammonium salts thereof. The pharmaceutically acceptable salts, can be prepared by methods well known in the art.

A group of compounds within the scope of formula Ia are those wherein X and Z are oxygen.

One group of compounds within the scope of formula Ia are those wherein X is imino and Z is oxygen.

Another group of compounds within the scope of formula Ia are those wherein X is oxygen and Z is sulfur.

One group of compounds within the scope of formula Ia are those of formula Ia-1

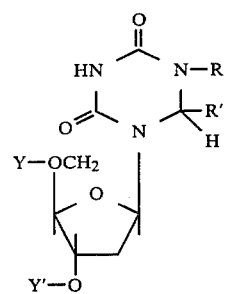

Ia-1 wherein R is selected from the group consisting of hydrogen, ethyl, n-propyl, isopropyl, cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen; including pharmaceutically acceptable salts thereof when Y is phosphono.

A group of compounds within the scope of formula Ia-1 are those wherein R' is hydrogen.

A group of compounds within the scope of formula Ia-1 are those wherein the Y and Y' are hydrogen.

A group of compounds with the scope of formula Ia-1 are those wherein Y, Y' and R' are hydrogen.

Another group of compounds within the scope of formula Ia-1 are those wherein Y and Y' are carboxacyl of from 1 through 18 carbon atoms and R' is hydrogen.

Another group of compounds within the scope of formula Ia-1 are those wherein Y is carboxacyl of from 1 through 18 carbon atoms; Y' and R' are hydrogen.

Still another group of compounds within the scope of formula Ia-1 are those wherein Y' is carboxacyl of from 1 through 18 carbon atoms; Y and R' are hydrogen.

A group of compounds within the scope of formula Ia are those of formula Ia-2

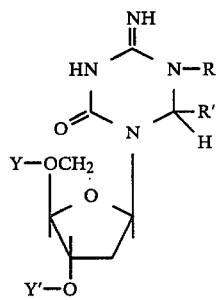

Wherein R is selected from the group consisting of hydrogen, methyl, ethyl, n-propyl, isopropyl, and cyclopropyl; R' is selected from the group consisting of hydrogen and lower alkyl of 1 through 4 carbon atoms; Y is selected from the group consisting of hydrogen, carboxacyl of from 1 through 18 carbon atoms, and phosphono; Y' is selected from the group consisting of carboxacyl of from 1 through 18 carbon atoms and hydrogen; and pharmaceutically acceptable salts thereof.

A group of compounds within the scope of formula Ia-2 are those wherein R' is hydrogen.

A group of compounds within the scope of formula Ia-2 are those wherein Y and Y' are hydrogen.

One group of compounds within the scope of formula Ia-2 are those wherein Y, Y' and R' are hydrogen.

Another group of compounds within the scope of formula Ia-2 are those wherein Y and Y' are carboxacyl of from 1 through 18 carbon atoms and R' is hydrogen.

Another group of compounds within the scope of formula Ia-2 are those wherein Y is carboxacyl of from 1 through 18 carbon atoms, Y' and R' are hydrogen.

Still another group of compounds within the scope of formula Ia-2 are those wherein Y' is carboxacyl of from 1 through 18 carbon atoms, Y and R' are hydrogen.

Another group of compounds within the scope of formula Ia are those of formula Ia-3

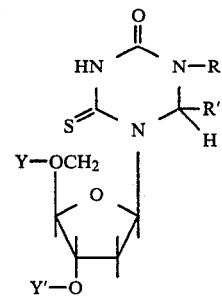

wherein R is selected from the group consisting of hydrogen, methyl, ethyl, n-propyl, isopropyl, and cyclopropyl; R' is selected from the group consisting of hydrogen and lower alkyl of 1 through 4 carbon atoms; Y is selected from the group consisting of hydrogen carboxacyl of from 1 through 18 carbon atoms, and phosphono; Y' is selected from the group consisting of carboxacyl of from 1 through 18 carbon atoms and hydrogen; including pharamaceutically acceptable salts thereof when Y is phosphono.

A group of compounds within the scope of formula Ia-3 are those wherein R' is hydrogen.

A group of compounds within the scope of formula Ia-3 are those wherein Y and Y' are hydrogen.

One group of compounds within the scope of formula Ia-3 are those wherein Y, Y' and R' are hydrogen.

Another group of compounds within the scope of formula Ia-3 are those wherein Y and Y' are carboxacyl of from 1 through 18 carbon atoms and R' is hydrogen.

Another group of compounds within the scope of formula Ia-3 are those wherein Y is carboxacyl of from 1 through 18 carbon atoms, Y' and R' are hydrogen.

Still another group of compounds within the scope of formula Ia-3 are those wherein Y' is carboxacyl of from 1 through 18 carbon atoms, Y and R' are hydrogen.

Another group of compounds within the scope of formula Ia are those of formula Ia-4.

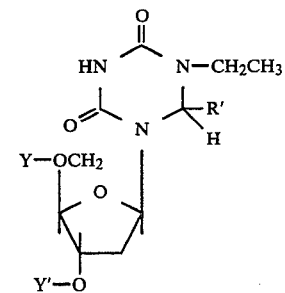

wherein R' is selected from the group consisting of hydrogen and lower alkyl of 1 through 4 carbon atoms; Y is selected from the group consisting of hydrogen, carboxyacyl of from 1 through 18 carbon atoms, and phosphono; and Y' is selected from the group consisting of carboxacyl of from 1 through 18 carbon atoms and hydrogen; including pharmaceutically acceptable salts thereof when Y is phosphono.

A group of compounds within the scope of formula Ia-4 are those wherein R' is hydrogen.

Another group of compounds within the scope of formula Ia-4 are those wherein Y and Y' are hydrogen.

Another group of compounds within the scope of formula Ia-4 are those wherein Y and Y' are carboxyacyl of from 1 through 18 carbon atoms and R' is hydrogen.

Still another group of compounds within the scope of formula Ia-4 are those wherein Y' is carboxyacyl of from 1 through 18 carbon atoms; Y and R' are hydrogen.

Another group of compounds within the scope of formula Ia-4 are those wherein Y is carboxyacyl of from 1 through 18 carbon atoms; and Y' and R' are hydrogen.

For reason of brevity, compounds wherein Y'—O is in the threo configuration are not rendered in the same manner as compounds within the scope of formula Ia-1, Ia-2, Ia-3 and Ia-4, but the same illustrative scoping is intended.

The compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of formula Ia.

For oral administration either solid or fluid unit dosage forms can be prepared. For preparing solid compositions such as tablets, the compound of formula Ia is mixed with conventional ingredients such as talc, magnesium, stearate, dicalcium phosphate, magnesium aluminum silicate, starch, lactose, acacia, methylcellulose, and functionally similar materials as pharmaceutical diluents or carriers. The tablets can be coated or left uncoated. Suitable coatings include a sealing coat of shellac, a carbohydrate coating (such as sugar or methylcellulose), and a lipid polish coating such as carnauba wax. Special coatings can comprise (a) lipid-type coatings of a semi-permeable nature for delaying absorption of the active ingredient to provide sustained action or (b) enteric substances, such as styrene-maleic acid copolymer and cellulose acetate phthalate, to resist release of the active ingredient in the stomach and permit release in the upper intestine. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with corn oil, light liquid petrolatum or other inert oil.

Fluid unit dosage forms for oral administration such as emulsions, syrups, elixirs, and suspensions can be prepared. Emulsions can be oil-in-water or water-in-oil type and contain the active ingredient in the required amount with acceptable emulsifying agents, such as gum acacia, gum tragacanth, and the like. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent. Suspensions can be prepared of the insoluble forms in aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound depending on the form and concentration used, can be either suspended or dissolved in the vehicle. In preparing solutions a water-soluble compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the injectable solution prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound. For the treatment of animals by oral administration, the active ingredient is conveniently prepared in the form of a food premix. The food premix can comprise the active ingredient in admixture with an edible diluent such as starch, oatmenal, flour, calcium carbonate, talc, dried fish meal and like non-toxid, orally-acceptable diluents. The prepared premix is then added to the regular feed, thereby supplying the included medication to the animal in the course of feeding.

In addition to the administration of the compound of the formula Ia as the principal active ingredient of compositions for the treatment of the conditions described herein, the said compound can be included with other types of compounds to obtain advantageous combinations of properties. Such combinations include a compound of the formula Ia with analgesics such as aspirin, sodium salicylate, (acetylsalicylic acid)-anhydride, N-acetyl-p-aminophenol and salicylamide; antihistamines, such as chlorpheniramine maleate, diphenhydramine, promethazine, pyrathiazine, and the like; sulfas, such as sulfadiazine, sulfamethazine, sulfamerazine, sulfacetamide, sulfadimethyloxazole, sulfamethizole, and the like; antifungals such as undecylenic acid, sodium, propionate, salicylanilide, sodium caprylate, and hexetidine; antivirals such as cytarabine compound or amantidine; and the vitamins.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosge forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, troches, suppositories, powder packets, granules, wafers, cachets, teaspoonsful, tablespoonsful, droppersful, ampuls, vials, segregated multiples of any of the foregoing, and other forms as herein described.

The dosage of the compound for treatment depends on the route of administration; the age, weight, and condition of the patient, and the particular disease to be treated. For adults, a daily dosage comprises from about 300 to about 3200 mg./kg. of compound, embraces the effective range for the treatment of most susceptible viral infections. The dose can be administered once per day or in increments throughout the day in order that an antiviral concentration of compound is present in the blood for a minimum of at least 8 hours of the day. For example, a range of about $1\times10^{-4}$M to about $4\times10^{-4}$M of 1-(2-deoxy-$\beta$-D-ribofuranosyl)-5-ethyl-5,6-dihydro-s-triazine-2,4-(1H,3H)-dione in the blood can be used to treat infections due to herpes simplex type 1 virus. The blood levels can be determined after administration of a suitable radiolabeled form of the compound and determining the level of the compound at appropriate times after compound administration. A method useful for such determinations is that described by G. L. Neil et al., published in Biochemical Pharmacology, 20, 3295-3308 (1971).

In general, a dose of from about 300 mg./kg./day to about 3200 mg./kg./day embraces the effective range and can be used for the systemic treatment of susceptible viral infections in humans and animals, including but not limited to, mammals and avians, e.g., cattle cats, dogs and poultry. More specifically, a dose of from about 300 mg./kg./day to about 1600 mg./kg./day can be used for the systemic treatment of infections due to herpes simplex type 1 virus.

The compound is formulated with a suitable pharmaceutical carrier in unit dosage form for convenient and effective administration in the preferred embodiments of this invention, the dosage units contain compound in 25, 50, 100, 200, 250, 500, and 1000 mg. amounts for systemic treatment and in 5 to 65% w/v for parenteral preparations.

The administration of the compositions of the present invention to humans and animals provides a method for the treatment of susceptible DNA viral infections.

For example, the process can be used for the treatment of viral infections due to susceptible herpes virus. Herpes viruses include, for example herpes simplex type 1, varicella-zoster and cytomegalovirus as well as infectious bovine rhinotracheitis virus Marek's disease virus, canine herpes virus and feline rhinotracheitis virus. However, some Herpes viruses such as pseudorabies and equine abortion virus have been tested in vitro against 1-(2-deoxy-$\beta$-D-ribofuranosyl)-5-methyl-5,6-dihydro-s-triazine-2,4-(1H,3H)-dione and 1-(2-deoxy-$\beta$-D-ribofuranosyl)-5-ethyl-5,6-dihydro-s-triazine-2,4-(1H,3H)-dione and, to date, have been demonstrated to be refractory or at best only slightly inhibited, i.e. susceptible. To date, treatment of vaginal herpes simplex virus type 2 infection in mice with 1-(2-deoxy-$\beta$-D-ribofuranosyl)-5-methyl-5,6-dihydro-s-triazine-2,4(1H,3H)-dione or 1-(2-deoxy-$\beta$-D-ribofuranosyl)-5-ethyl-5,6-dihydro-s-triazine-2,4-(1H,3H)-dione, given by subcutaneous injection at doses such as those shown in Table 1, page 65, has resulted in extensions of mean survival times but the number of mice surviving the infection was not greatly or significantly enhanced. Herpes simplex type 2 virus (HSV-2) has been tested in vitro against 1-(2-deoxy-$\beta$-D-ribofuranosyl)-5-methyl-5,6-dihydro-s-triazine-2,4-(1H,3H)-dione, 1-(2-deoxy-$\beta$-D-ribofuranosyl)-5-ethyl-5,6-dihydro-s-triazine-2,4-(1H,3H)-dione, 1-(2-deoxy-$\beta$-D-ribofuranosyl)-5-n-propyl-5,6-dihydro-s-triazine-2,4-(1H,3H)-dione, 1-(2-deoxy-$\beta$-D-ribofuranosyl)-5-isopropyl-5,6-dihydro-s-triazine-2,4-(1H,3H)-dione, 1-(2-deoxy-$\beta$-D-ribofuranosyl)-5-cyclopropyl-5,6-dihydro-s-triazine-2,4-(1H,3H)-dione, and has been demonstrated to be susceptible.

Following examples are illustrative of the process and products of the present invention but are not to be construed as limiting.

Example 1 Capsules

Two hundred and fifty two-piece hard gelatin capsules for oral use, each containing 1000 mg. of 1-(2-deoxy-$\beta$-D-ribofuranosyl)-5-ethyl-5,6-dihydro-s-triazine-2,4-(1H,3H)-dione are prepared from the following types and amounts of materials:

| | |
|---|---|
| 1-(2-deoxy-$\beta$-D-ribofuranosyl)-5-ethyl-5,6-dihydro-s-triazine-2,4-(1H,3H)-dione | 250 Gm. |
| Talc | 50 Gm. |
| Magnesium stearate | 25 Gm. |

The materials are thoroughly mixed and then encapsulated in the usual manner.

The foregoing capsules are useful for the systemic treatment of herpes simplex type 1 viral infections in adult humans by the oral administration of 7 capsules every 2 hours.

Using the procedure above, capsules are similarly prepared containing the compound in 25, 50, 100, 250 and 500 mg. amounts by substituting 6.25, 12.5, 25, 62.5 and 125 Gm. of compound for the 250 Gm. used above.

Example 2 Tablets

One thousand tablets for oral use, each containing 500 mg. of 1-(2-deoxy-$\beta$-D-ribofuranosyl)-5-ethyl-5,6-dihydro-s-triazine-2,4-(1H,3H)-dione are prepared from the following types and amounts of materials.

| | |
|---|---|
| 1-(2-deoxy-$\beta$-D-ribofuranosyl)-5-ethyl-5,6-dihydro-s-triazine-2,4-(1H,3H)-dione | 500 Gm. |
| Lactose | 125 Gm. |
| Corn starch | 65 Gm. |
| Magnesium stearate | 5 Gm. |
| Light liquid petrolatum | 3 Gm. |

The ingredients are thoroughly mixed and slugged. The slugs are broken down by forcing through a number sixteen screen. The resulting granules are then compressed into tablets, each tablet containing 500 mg. of compound.

The foregoing tablets are useful for systemic treatment of herpes simplex type 1 viral infections in adult humans by oral administration of 14 tablets every 2 hours. In severe conditions, 10 to 20 tablets can be administered every 1 hours.

Using the above procedure, except for reducing the amount of compound to 200 Gm., tablets containing 200 mg. of 1-(2-deoxy-$\beta$-D-ribofuranosyl)-5-ethyl-5,6-dihydro-s-triazine-2,4-(1H,3H)-dione are prepared.

Example 3

Granules

2367 Gm. of a granulation suitable for reconstitution with water prior to use is prepared from the following types and amounts of ingredients:

| | |
|---|---|
| 1-(2-deoxy-$\beta$-D-ribofuranosyl)-5-ethyl-5,6-dihydro-s-triazine-2,4-(1H,3H)-dione | 150 Gm. |
| Sucrose, powdered | 2155 Gm. |
| Flavor | 60 Gm. |

| -continued | |
|---|---|
| Sodium metabisulfite | 2 Gm. |

The ingredients are mixed together until thoroughly blended. The powder mixture is wetted with water and forced through a screen to form granules. The granules are dried and 23.67 Gm. filled into 60 ml. bottles. Prior to use, sufficient water is added to the granules to make 60 ml. of composition.

The foregoing composition (125 mg./5 ml.) is useful for systemic treatment of herpes simplex type 1 viral infections particularly in children at a dose of 5–10 teaspoonfuls (5 ml.) at 2 hours intervals during an 8 hour time span daily.

Example 4 Oral Syrup 1000 ml. of an aqueous preparation for oral use, containing in each 5 ml. dose, 250 mg. of 1-(2-deoxy-$\beta$-D-ribofuranosyl)-5-ethyl-5,6-dihydro-s-triazine-2,4-(1H,3H)-dione is prepared from the following types and amounts of ingredients:

| | |
|---|---|
| 1-(2-deoxy-$\beta$-D-ribofuranosyl)-5-ethyl-5,6-dihydro-s-triazine-2,4-(1H,3H)-dione | 50 Gm. |
| Citric acid | 2 Gm. |
| Benzoic acid | 1 Gm. |
| Sucrose | 700 Gm. |
| Tragacanth | 5 Gm. |
| Lemon oil | 2 Gm. |
| Deionized water, q.s. | 1000 ml. |

The citric acid, benzoic acid, sucrose, tragacanth, and lemon oil are dispersed in sufficient water to make 850 ml. of solution. The 1-(2-deoxy-$\beta$-D-ribofuranosyl)-5-ethyl-5,6-dihydro-s-triazine-2,4-(1H,3H)-dione is stirred into the syrup until uniformly distribute. Sufficient water is added to make 1000 ml.

The composition so prepared is useful in the systemic treatment of infection due to Herpes simplex virus type 1 in adult humans at a dose of 14–21 teaspoonfuls 6–12 times a day. In severe conditions, 12.4 tablespoonfuls (15 cc.) can be administered 8–12 times a day.

Example 5 Parenteral Solution

A sterile aqueous solution for parenteral use, containing in 1 ml., 100 mg. of 1-(2-deoxy-$\beta$-D-ribofuranosyl)-5-ethyl-5,6-dihydro-s-triazine-2,4-(1H,3H)-dione is prepared from the following types and amounts of materials:

| | |
|---|---|
| 1-(2-deoxy-$\beta$-D-ribofuranosyl)-5-ethyl-5,6-dihydro-s-triazine-2,4-(1H,3H)-dione | 1000 Gm. |
| Methylparaben | 2.5 Gm. |
| Propylparaben | 0.17 Gm. |
| Water for injection q.s. | 1000 ml. |

All of the ingredients, except the compound, are dissolved in the water and the solution sterilized by filtration. To the sterile solution is added the sterilized 1-(2-deoxy-$\beta$-D-ribofuranosyl)-5-ethyl-5,6-dihydro-s-triazine-2,4-(1H,3H)-dione and the final solution is filled into sterile vials and the vials sealed.

The foregoing composition is useful for systemic treatment of herpes simplex type 1 viral infections in adult humans by intravenous administration of 9 ml. every 2 hours.

Example 6 Animal Feed

1000 Gm. of a feed mix is prepared from the following types and amounts of ingredients:

| | |
|---|---|
| 1-(2-deoxy-$\beta$-D-ribofuranosyl)-5-ethyl-5,6-dihydro-s-triazine-2,4-(1H,3H)-dione | 10 Gm. |
| Soybean meal | 400 Gm. |
| Fish meal | 400 Gm. |
| Wheat germ oil | 50 Gm. |
| Sorghum molasses | 140 Gm. |

The ingredients are mixed together and pressed into pellets.

The composition can be fed to laboratory animals, i.e., rats, mice, guinea pigs, and rabbits for prophylaxis during shipping.

For larger animals the composition can be added to the animals regular feed in an amount calculated to give the desired dose.

The foregoing composition can be used for the treatment of Marek's disease in chickens by the addition of the composition to the animals regular feed in an amount calculated to give 300–3200 mg./kg./day.

Example 7

Following the procedure of each of the preceeding Examples 1 through 6, each of the compounds of formula Ia, as disclosed herein can be substituted in an equimolar amount for 1-(2-deoxy-$\beta$-D-ribofuranosyl)-5-ethyl-5,6-dihydro-s-triazine-2,4-(1H,3H)-dione shown in the examples to provide similar therapeutic properties.

Compounds of formula Ia are obtained by reacting a blocked-pentofuranosyl halide with a mono- or disilylated compound of the formulae

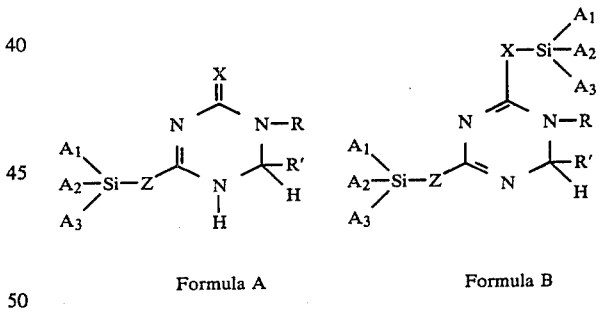

Formula A          Formula B wherein R, R', X and Z have the above indicated meanings, and $A_1$, $A_2$, and $A_3$ represent lower alkyl groups of 1 to 4 carbon atoms, and then splitting off the blocking groups; if desired.

5,6-Dihydro-5-(R)-6-(R')-s-triazines of the formula

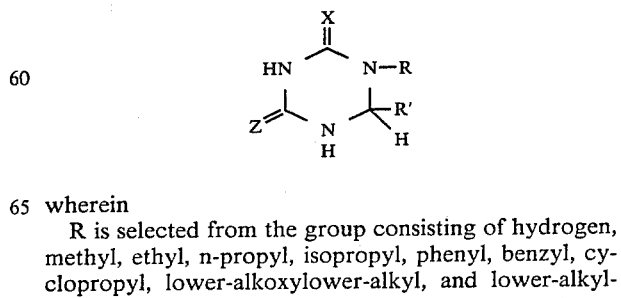

wherein

R is selected from the group consisting of hydrogen, methyl, ethyl, n-propyl, isopropyl, phenyl, benzyl, cyclopropyl, lower-alkoxylower-alkyl, and lower-alkylthiolower-alkyl, R' is selected from the group consisting of hydrogen and lower alkyl; X is selected from the group consisting of oxygen, imino, lower-alkylimino and lower-acylimino; and Z is selected from the group consisting of oxygen and sulfur; are mono- or disilylated by reaction with a trialkylsilyl halide, a trialkylsilylacetamide, a trimethylsilylamine, e.g., hexamethyldisilazane, to form the corresponding mono-silyl compounds of formula A or the corresponding di-silyl compounds of formula B.

The process described, comprises reacting a monosilyl compound of formula A with a 2-deoxy-3,5-blocked-D-pentofuranosyl halide in the presence of a Lewis acid at an initial temperature of about minus (−) 25° C., with subsequent warming to about 25° C.

A di-silyl compound of formula B can also be reacted with a 2-deoxy-3,5-blocked-D-pentofuranosyl halide in the presence of a Lewis acid at an initial temperature of about minus (−) 25° C. with subsequent warming to about 25° C. When the trialkylsilyl halide is used, an acid acceptor is included in the reaction mixture comprising a suitable reaction medium as is known in the art; see *Silylation of Organic Compounds,* Pierce Chemical Co., Rockford; Ill. (1968) and Chem. Pharm. Bull., 12, p. 352 (1964). In the practice of this invention, pyridine was successfully employed. The silylated 5,6-dihydro-s-triazine bases are recovered for further reaction with the blocked pentofuranosyl halide by conventional methods as described by the preparations herein.

The sugar and the silylated base are reacted in the presence of a Lewis acid such as stannic halide, e.g., stannic chloride or bromide, and a solvent medium such as benzene, ethylene dichloride, toluene, chloroform, acetonitrile (preferred), nitromethane, dioxane and tetrahydrofuran. Mercuric bromide (preferably mixed with a molecular sieve, Linde Type 3A or 4A) or silver perchlorate can also be used as catalyst. The initial reaction is effected at temperatures around minus (−) 25° C. Later, the reaction temperature is increased to about 25° C. as described.

The "blocked" 2-deoxypentofuranosyl halide reactants include especially the bromo- and chloro-halides with blocking groups, i.e. a carboxacyl protective group as commonly used in sugar chemistry. Ordinarily, the blocking groups will be acetyl, toluoyl or benzoyl, but can be any equivalent protective carboxacyl group. The method of preparing the blocked sugar halide reactants is conventional, e.g., reacting the sugar with an alcohol in the presence of acid, protecting the free OH-groups with a suitable blocking group and forming the sugar halide by treatment with anhydrous, hydrogen halide in an organic solvent. The function of the blocking group is to protect the hydroxyl groups during the reaction.

Illustrative sugar halides are 1-(2-deoxy-3,5-di-O-toluoyl-D-ribofuranosyl)-chloride and 1-(2-deoxy-3,5-di-O-toluoyl-D-xylofuranosyl)-chloride.

The intermediate 1-(2-deoxy-3,5-di-O-acyl-β-D-ribofuranosyl)-5,6-dihydro-5(R)-(R')-s-triazines are recovered by conventional techniques such as solvent extraction, precipitation, filtration, crystallization and chromatography. The blocking groups are removed as described in order to obtain the object compounds 1-(2-deoxy-β-D-pentofuranosyl)-5,6-dihydro-5(R)-6(R')-s-triazines.

The free nucleosides of the invention, compounds according to formula Ia wherein Y and Y' are hydrogen, can be acylated by standard procedures utilizing an acid halide or anhydride of an appropriate carboxylic acid including, for example, acetic anhydride, acetyl chloride, palmityl chloride, benzoyl chloride and succinic anhydride.

Various acylates of the free nucleosides of the invention can be made, and these acylates are useful to upgrade the free nucleosides. By following the procedure of Preparation 6, Part B, the 3',5'-di-esters are formed.

The 5'-mono-esters can be formed by standard procedures using a minimum amount of acylating agent, see, e.g. Preparation 10, Part B.

The 3'-mono-esters can be formed by tritylating the free nucleoside to give the 5'-trityl derivative, acylating with the acid halide or anhydride of an appropriate carboxylic acid such as those disclosed in U.S. Pat. No. 3,426,012, Columns 5 and 6, to give the 3'-mono-ester 5'-trityl derivative, which then can be converted to the 3'-mono-ester by removal of the trityl group.

Phosphorylation is readily accomplished by the methods described by D. Mitsunoku, K. Kato, and J. Kimura in Jour. Am. Chem. Soc. 91, p. 6510 (1969). After removal of the 3'-O-acyl group there are obtained 5'-phosphates according to the invention that have the desired anti-viral activity.

A preferred method of acylating the 3'-position is to first form an ether at the 5'-position with tert-butyldimethylsilyl chloride as described in Preparation 10, Part A. Acylation at the 3'-position is then accomplished as described in Preparation 10, Part B to obtain, e.g., 1-(5-O-tert-butyldimethylsilyl-3-O-lauroyl-2-deoxy-D-ribofuranosyl)-5-methyl-5,6-dihydro-s-triazine-2,4(1H,3H)-dione which is disilylated with tetra-n-butyl ammonium fluoride in tetrahydrofuran as in Preparation 10, Part C.

The following Preparations are to be construed as merely illustrative of compounds of Formula Ia and means of preparing said compounds, and not limitative of the remainder of the disclosure.

Preparation 1 Synthesis of precursor 5-ethyl-5,6-dihydro-s-triazine-2,4(1H,3H)-dione Part A Ethylbiuret To a quantity [1.0 kg. (7.56 mole)] of ethyl allophanate is added 2.3 l of 70 percent aqueous ethylamine. The reaction vessel is flushed with nitrogen gas in order to remove the oxygen present, and the reaction mixture is heated at temperatures in the range of 35° C. to 49° C. for 23 hours. The solution obtained is concentrated by removing much of the water and excess ethylamine by evaporation under reduced pressure and 45° C. A slurry results, which is cooled to 5° C. and filtered. The filter cake obtained is washed with 200 ml. of ice-cold, absolute ethanol. The washed crystals are dried under reduced pressure at 60° C. to give 802 gm. of ethylbiuret and starting ethyl allophanate. The 802 gm. quantity is again reacted with 2250 ml. of the 70 percent aqueous ethylamine diluted with an equal volume of water (2250 ml.). This reaction mixture is heated with stirring at 60° C. for 18 hours under a nitrogen atmosphere, and again much of the water an ethylamine is removed by evaporation under reduced pressure. The final volume is 1800 ml. The slurry thus obtained is cooled to 5° C. and filtered. After washing the white filter cake with icewater and drying under reduced pressure at 50° C., there is obtained 597 gm. (62.69 percent yield) of the desired ethylbiuret having a melting point of 158.5° to 160° C.

Part B 1-Ethyl-5-azauracil

The ethylbiuret prepared in Part A, above, [592 gm., 4.7 mole] is dispersed in 24 l. absolute ethanol and 1.6 l. benzene. This reaction mixture is heated to the reflux temperature and 3.5 l. of solvent medium is removed by distillation. The solution is cooled to 60° C. and 2090 gm. of a 25 percent solution of sodium methoxide in methanol is slowly added over an interval of five minutes. That addition is followed by the addition of 820 gm. of ethylformate. This reaction mixture is heated at the reflux temperature for three (3) hours, whereupon the solution is cooled to 38° C. and concentrated hydrochloric acid is added slowly until the pH of the solution is 2. To the acidified solution is added more (3.4 l.) benzene. Then 2.l. of the solvent medium is removed by distillation under reduced pressure and 50° C. The mixture is then heated to 75° C. and filtered in order to remove the sodium chloride produced by the reaction. The filter cake of salt is washed with hot absolute ethanol and the washings are added to the filtrate. The volume of the combined filtrate and absolute ethanol washings is reduced to 5 l. by evaporation under reduced pressure at 50° C. The resulting concentrate is cooled at 5° C. for 18 hours while crystals form. The crystals are collected on a filter and washed with cold (5°) ethanol. The washed crystals are dried in an oven under reduced pressure at 50° C. for 18 hours. There is thus obtained 408 gm. of crude product having a melting point at 137° to 139° C. A further purification is achieved by dissolving the 408 gm. in 4 l. methanol at reflux temperature. This solution is concentrated by allowing the methanol to evaporate to a volume of 2 l. while being heated on a steam bath. The concentrated solution is allowed to cool slowly to 25° C. It is then chilled to 5° C. for two hours. The crystals that form are collected on a filter and the filter cake is washed with ice-cold methanol. After drying there is obtained 389 gm. (58.7 percent yield) of 1-ethyl-5-azauracil having a melting point of 141° to 142° C. A second crop of crystals is recovered from the mother liquor after further concentration and cooling.

An analytical sample is prepared by recrystallizing from tetrahydrofuran. A 1.0 gm. sample is dissolved in 50 ml. and filtered while hot. The filtrate is concentrated to a volume of 25 ml. by evaporation of solvent medium and 50 ml. toluene is added. This solution is again concentrated to a volume of 25 ml. by evaporating the solvents on a steam bath. This concentrate is cooled to 25° C. and crystals formed. The crystals are collected on a filter, the filter cake is rinsed with Skellysolve B ® essentially n-hexane, B.P. 60° C.–68° C. Skellysolve Oil Co., Inc. After drying the crystals in air, there are obtained 0.8 gm. of pure 1-ethyl-5-azauracil having a melting point of 144° to 145° C.

Analysis:
Calc'd for $C_5H_7N_3O_2$: C, 42.55; H, 5.00; N, 29.78. Found: C, 42.33; H, 508; N, 29.36.

Part C The desired precursor, 5-ethyl-5,6-dihydro-s-triazine-2,4-(1H,3H)-dione.

To a quantity [370 gm., 2.62 mole] of the 1-ethyl-5-azauracil prepared in Part. B, above is added 2200 ml. water and 40 gm. of 5 percent rhodium on activated charcoal. This mixture is put of a Parr hydrogenation chamber and hydrogen gas is introduced to a pressure of 50 pounds per square inch (p.s.i.) and the reaction system is heated to 100° C. When uptake of hydrogen ceases, the hydrogen pressure is increased to 200 p.s.i and held there for 18 hours. The hydrogenated reaction mixture is rinsed out of the reaction chamber with hot water, filtered while hot, and the filter is washed with one l. of water at 80° C. The aqueous solution is set aside at 25° C. for 18 hours, during which interval crystals form. The crystals are collected on a filter and dried at 50° C. under reduced pressure. There is thus obtained 70 gm. of 5-ethyl-5,6-dihydro-s-triazine-2,4-(1H,3H)-dione having a melting range between 220° C. and 224° C.

The mother liquor is concentrated by evaporating water until a slurry is obtained and the volume is 500 ml. After cooling, the crystals are collected on a filter and dried at 70° C. under reduced pressure. There is thus obtained 159 gm. of a second crop. These crystals are dissolved in 4.5 l. of methanol which has been heated to boiling. This methanolic solution is chilled to 5° C., set aside for 18 hours at that temperature, and then filtered. The filter cake is washed with 300 ml. of ice-cold methanol and dried at 50° C. under reduced pressure. There is thus obtained 77 gm. of product having a melting range between 220° and 224° C.

The filtrate is concentrated to a one l. volume by evaporating methanol. There is thus obtained 15.46 gm. of product which has a melting range between 211° and 218° C. After combining the 70 gm., 77 gm., and 15 gm. crops by dissolving them in 4 l. of boiling methanol, there is obtained, after chilling, an analytical sample weighing 138 gm. which has a melting range between 221° and 225° C.

Analysis: Calc'd for $C_5H_8N_3O_2$: C, 41.95; H, 6.34; N, 29.36. Found: C, 41.89; H, 6.55; N, 29.31.

Preparation 2 Synthesis of known precursor 5,6-dihydro-5-methyl-s-triazine-2,4-(1H,3H)-dione Part A Methylbiuret A reaction mixture consisting of 200 gm. (1.5 mole) ethyl allophanate and 800 ml. of 40 percent aqueous methylamine is introduced into a two l. flask and the flask is loosely stoppered. After stirring for from 3 to 5 hours a clear solution is obtained. Stirring is continued for a total of 18 hours. The reaction medium is then allowed to evaporate until the odor of methylamine is no longer noticeable. The aqueous slurry thus obtained is filtered and the aqueous filtrate is discarded. The white solid on the filter is recrystallized from ethanol which contained a small proportion of methanol. There is thus obtained 125 gm. (71 percent yield) of methylbiuret as white crystals having a melting point of 173° to 175° C.

Part B 1-Methyl-5-azauracil

A reaction mixture consisting of 70.2 gm. (0.6 mole) of the 1-methylbiuret prepared in Part A above, 3.5 l. absolute ethanol, and 200 ml. benzene is heated to the reflux temperature with stirring in a 5-l., three-necked flask fitted with a reflux condenser, a stirrer, and thermometer. The top of the condenser is fitted with a nitrogen outlet, but no water is run through the condenser. After removing the nitrogen outlet, 200 ml. of the medium is allowed to distill through the condenser. The reaction mixture is then cooled to 60° C., before 28 gm. (1.2 mole) of sodium metal is added slowly over an interval of five (5) minutes. A white solid precipitates, but stirring is continued until all the sodium is dissolved. At this point, 104 gm. (1.4 mole) of ethyl formate is added in one portion and the reaction mixture is again heated to the reflux temperature (about 75° C.) and refluxed for three (3) hours. The reaction mixture is cooled to about 30° C. and hydrogen chloride gas is blown over the surface until an acid pH is attained. The reaction mixture is again heated at the reflux temperature for 15 minutes. The hot mixture is filtered through a diatomaceous earth filter and the filter is washed with hot ethanol. The filtrate and washings are concentrated to a volume of 200 to 300 ml. by removing medium by evaporation under reduced pressure. The concentrate is cooled to 5° C. and set aside at that temperature for several hours for crystallization. The crystals are collected on a filter and washed with cold ethanol. After, drying the crystals under reduced pressure there is obtained 69 gm. (90% yield) of 1-methyl-5-azauracil having a melting range from 200° to 205° C. A sample recrystallized three times from ethanol has a melting point of 213° to 214° C.

Part C The desired known precursor, 5,6-dihydro-5-methyl-s-triazine-2,4-(1H,3H)-dione A hydrogenation mixture consisting of 203.5 gm. (1.6 moles) of the 1-methyl-5-azauracil prepared in Part B, above, 7 teaspoons of Raney Nickel, and 8 l. ethanol in a five-gallon autoclave is subjected to 750 p.s.i. hydrogen pressure at 125° C. for an interval of 12 hours. The hydrogen is flushed out of the chamber with nitrogen gas and the reaction mixture is siphoned out of the chamber into a five-gallon carboy. The walls of the chamber are washed down with water and these washings are siphoned into the carboy. The carboy is then flushed with nitrogen (<20 p.s.i.) so as to force the medium through a filter stick onto a filter bed of Dicalite 4200 (diatomaceous earth). The solids are retained in the carboy substantially undisturbed. The medium is then sucked through the dicalite filter under reduced pressure until 1 inch of liquid remains. The solids retained in the bottom of the carboy are now mixed with two (2) liters water and 500 ml. Dicalite 4200 and this mixture is added to the filter cake. The filter cake is then washed with water. The filtrate and washings are combined and the water is removed to a volume of 1200 ml. by evaporation under reduced pressure, 20 mm mercury, and 50° C. temperature. The concentrate thus obtained is heated to 90° C., and 95% aqueous ethanol is added to a volume of two liters. Upon cooling, crystallization occurs. The crystals are collected on a filter and dried. There is thus obtained 120 gm. (59% yield) of 5,6-dihydro-5-methyl-s-triazine-2,4-(1H,3H)-dione having a melting point of 252° to 254° C.

Preparation 3 Synthesis of precursor
3,4,5,6-tetrahydro-4-imino-5-methyl-s-triazine-2-(1H)-one Part A New antecedent, 5,6-dihydro-5-methyl-4-thio-s-triazine-2-(1H,3H)-one 12.90 gm. of 5,6-dihydro-5-methyl-s-triazine-2,4-(1H,3H)-dione (prepared as in Preparation 2, Part C, above) is added to 500 ml. of pyridine. With protection from moisture, 33.0 ml. of Bistrimethylsilyltrifluoroacetamide is added and the reaction mixture is stirred at 25° C. for 18 hours. This reaction mixture is poured into 7.50 gm. phosphorus pentasulfide from which pyridine has been distilled (under vacuum) twice; heated at reflux, with stirring, for 42 hours. After first cooling to 25° C., the residue is evaporated under vacuum to dryness and tritrated with chloroform and the resulting solids washed with chloroform to yield 9.45 gm. of 5,6-dihydro-5-methyl-s-triazine-2,4-(1H,3H)-dione. The chloroform solution is evaporated to dryness and the resulting residue chromatographed on 1.4 kg. silica gel using 2% methanol in chloroform as eluent. Fractions are collected with rf. 0.7 (in 15% methanol/chloroform) to give 395 mg. of 5,6-dihydro-5-methyl-2-thio-s-triazine-2,4-(1H,3H)-dione and those fractions containing material with rf. 0.65 (15% methanol/chloroform) to yield 92 mg. of 5,6-dihydro-5-methyl-4-thio-s-triazine-2,4-(1H,3H)-dione, melting point 273°–274° C.

Analysis: Calc'd. for $C_4H_7N_3OS$ (145.18): C, 33.09; H, 4.86; N, 28.94; S, 22.08. Found: C, 33.01; H, 5.20; N, 29.18; S, 21.67.

Following the same procedure, but substituting
5,6-dihydro-s-triazine-2,4-(1H,3H)-dione,
5,6-dihydro-5-ethyl-s-triazine-2,4-(1H,3H)-dione,
5,6-dihydro-5-n-propyl-s-triazine-2,4-(1H,3H)-dione,
5,6-dihydro-5-cyclopropyl-s-triazine-2,4-(1H,3H)-dione,
5,6-dihydro-5-isopropyl-s-triazine-2,4-(1H,3H)-dione,
5,6-dihydro-5-methoxymethyl-s-triazine-2,4-(1H,3H)-dione, and
5,6-dihydro-5-methylthiomethyl-s-triazine-2,4-(1H,3H)-dione, for the 5,6-dihydro-5-methyl-s-triazine-2,4-(1H,3H)-dione, there are prepared the corresponding
5,6-dihydro-4-thio-s-triazine-2-(1H,3H)-one,
5,6-dihydro-5-ethyl-4-thio-s-triazine-2-(1H,3H)-one,
5,6-dihydro-5-n-propyl-4-thio-s-triazine-2-(1H,3H)-one,
5,6-dihydro-5-cyclopropyl-4-thio-s-triazine-2-(1H,3H)-one,
5,6-dihydro-5-isopropyl-4-thio-s-triazine-2-(1H,3H)-one,
5,6-dihydro-5-methoxymethyl-4-thio-s-triazine-2-(1H,3H)-one, and
5,6-dihydro-5-methylthiomethyl-4-thio-s-triazine-2-(1H,3H)-one, respectively.

Part B New precursor, 3,4,5,6-tetrahydro-4-imino-5-methyl-s-triazine-2-(1H)-one

A cold reaction mixture is prepared by mixing 0.725 gm. (0.005 mole) of the 5,6-dihydro-5-methyl-4-thio-s-triazine-2-(1H,3H)-one prepared as in Part A, above, and 25 ml. of a saturated methanolic solution of ammonia which has been cooled to 0° C. The reaction mixture is put in a stainless steel pressure chamber and heated at 105° C. for 72 hours. After cooling and filtering, the filter cake is washed with ice-cold methanol and dried under reduced pressure at 50° C. and the product collected. The filtrate and methanol washings are combined and the methanol is removed by evaporation. The residue thus obtained is triturated with 5 ml. methanol at 25° C. to give additional product. Both crops of product are combined and dissolved in 20 ml. of boiling ethanol, water being added until solution is complete. The aqueous ethanol solution is then cooled to 5° C. and refrigerated at that temperature for 18 hours. The crystals that are formed are collected on a filter and washed with cold ethanol at 5° C. The washed crystals are dried under reduced pressure at 50° C. to give 3,4,5,6-tetrahydro-4-imino-5-methyl-s-triazine-2-(1H)-one.

Following the procedure of Preparation 3, Part B, but substituting
5,6-dihydro-4-thio-s-triazine-2-(1H,3H)-one,
5,6-dihydro-5-ethyl-4-thio-s-triazine-2-(1H,3H)-one,
5,6-dihydro-5-n-propyl-4-thio-s-triazine-2-(1H,3H)-one,
5,6-dihydro-5-cyclopropyl-4-thio-s-triazine-2-(1H,3H)-one,
5,6-dihydro-5-isopropyl-4-thio-s-triazine-2-(1H,3H)-one,
5,6-dihydro-5-methoxymethyl-4-thio-s-triazine-2-(1H,3H)-one, and
5,6-dihydro-5-methylthiomethyl-4-thio-s-triazine-2-(1H,3H)-one for the 5,6-dihydro-5-methyl-4-thio-s- triazine-2-(1H,3H)-one, there are prepared the corresponding
3,4,5,6-tetrahydro-4-imino-s-triazine-2-(1H)-one,
3,4,5,6-tetrahydro-4-imino-5-ethyl-s-triazine-2-(1H)-one,
3,4,5,6-tetrahydro-4-imino-5-n-propyl-s-triazine-2-(1H)-one,
3,4,5,6-tetrahydro-4-imino-5-cyclopropyl-s-triazine-2-(1H)-one,
3,4,5,6-tetrahydro-5-isopropyl-4-imino-s-triazine-2-(1H)-one,
3,4,5,6-tetrahydro-5-methoxymethyl-4-imino-s-triazine- 2-(1H)-one, and
3,4,5,6-tetrahydro-5-methylthiomethyl-4-imino-s-triazine-2-(1H)-one, respectively.

Preparation 4 Preparation of
4-imino-4-N-acetyl-3,4,5,6-tetrahydro-5-methyl-s-triazine-2-(1H)-one To 1.28 gm 10 mm of 4-imino-5,6-dihydro-5-methyl-s-triazine-2-(1H,3H)-one is added 50 ml. of pyridine, followed by 10 mm of acetyl chloride at 25° C. for 18 hours. The reaction mixture evaporated to dryness and is the desired 4-imino-N-acetyl-3,4,5,6-tetrahydro-5-methyl-5-triazine-2-(1H)-is isolated by crystallization from methanol.

Preparation 5 Synthesis of precursor
2-deoxy-3,5-di-O-tuluoyl-D-ribofuranosyl chloride A reaction mixture consisting of 20 gm. (0.15 mole) 2-deoxy-D-ribose, 360 ml. methanol, and 20.0 ml. of a 1% solution of hydrogen chloride in methanol is stirred for one hour at 25° C. Pyridine is added to a slight excess, and the volatile components are then removed by evaporation under reduced pressure. The residue is dissolved in pyridine and the pyridine is evaporated under vaccum. The residue is dissolved in 125 ml. pyridine, and the solution is cooled to 0° C. While maintaining the temperature at 0° C. to 10° C., 50.0 gm. (0.33 mole) of p-toluoyl chloride is added. Afterwards, the reaction mixture is allowed to gradually warm to 25° C. while stirring is continued for about 16 hours. After this prolonged interval of stirring, the reaction mixture is again cooled to 0° C. and 400 ml. water is added followed by 200 ml. chloroform. The addition of the water decomposed the excess p-toluoyl chloride. During addition the temperature is not permitted to rise above 10° C. The mixture is stirred for one hour, the organic and aqueous phases is allowed to separate, and the aqueous phase is recovered for purposes of extraction with two-150 ml. portions of chloroform. The combined original chloroform layer and chloroform extracts is washed with three-100 ml. portions of 3N sulfuric acid at 5° C., three-100 ml. portions of saturated aqueous sodium bicarbonate, and one 200 ml. portion of water. The washed chloroform solution is dried with anhydrous magnesium sulfate, and after removing the magnesium sulfate by filtration, the chloroform is removed by evaporation under reduced pressure. There is thus obtained 59.5 gm. of 1-methoxy-3,5-di-O-toluoyl-2-deoxy-D-ribose as a dark amber gum. To 73.5 gm. of 1-methoxy-3,5-di-O-toluoyl-2-deoxy-D-ribose is added 175 ml. diethyl ether and this ether solution is poured into 365 ml. of glacial acetic acid that has been saturated at 17° C. with anhydrous hydrogen chloride gas. The addition is optimally made at 0° C. to 5° C. With vigorous stirring at 0° C., additional hydrogen chloride gas is introduced until crystals form. Stirring is continued for 3 to 5 minutes before filtering. The filter cake is washed thoroughly with diethyl ether, and the washed crystals are dried under reduced pressure at 25° C. There is thus obtained 48 gm. (66% yeild) of 1-chloro-3,5-di-O-toluoyl-2-deoxy-D-ribose.

The crude title compound is purified by dissolving the above product in boiling carbon tetrachloride, chilling the solution immediately to minus (−) 10° C. and then setting it aside at 5° C. to 10° C. for 2 hours. The crystals of 1-chloro-3,5-di-O-toluoyl-2-deoxy-D-ribose are recovered on a filter.

Preparation 6 Preparation of
1-(2-deoxy-β-D-ribofuranosyl)-5-ethyl-5,6-dihydro-s-triazine-2,4-(1H,3H)-dione Part A Synthesis of the monosilylated precursor 5-ethyl-5,6-dihydro-2-O-(trimethylsilyl)-s-triazine-4-(3H)-one.

A reaction mixture consisting of 7.15 gm. (0.05 mole) of 5-ethyl-5,6-dihydro-s-triazine-2,4-(1H,3H)-dione prepared in Preparation 1, Part C, (above), 150 ml. hexamethyldisilazane, and a catalytic amount (3 mg.) of ammonium sulfate is heated at the reflux temperature for 48 hours. The volatiles are removed by evaporation under reduced pressure, and the residue thus obtained is held under reduced pressure for 18 hours. The 5-ethyl-5,6-dihydro-2-O-(trimethylsilyl)-s-triazine-4-(3H)-one is obtained as a white solid that gave an NMR spectrum deuterated chloroform (CDCl$_3$): NH at 7.9 δ and a ring CH$_2$ at 4.33 δ (S).

Part B Preparation of intermediates 1-(3,5-di-O-toluoyl-2-deoxy-(B-D-ribofuranosyl)-5-ethyl-5,6-dihydro-s-triazine-2,4-(1H,3H)-dione and 1-(3,5-di-O-toluoly-2-deoxy-α-D-ribofuranosyl)-5-ethyl-5,6-dihydro-s-triazine.

To a solution consisting of the 2-O-trimethylsilyl ether of 5-ethyl-5,6-dihydro-s-triazine-2,4-(1H,3H)-dione prepared in Part A above, and 625 ml. of reagent grade acetonitrile is chilled, in a reaction vessel freed of moisture and oxygen by flushing with nitrogen, to a temperature of minus (−) 25° C., before 3.75 ml. of fuming, anhydrous stannic chloride is injected. This reaction mixture is stirred for five (5) minutes at the minus (−) 25° C. temperature whereupon 10.0 gm. (0.025 mole) of 3,5-di-O-toluoyl-2-deoxy-D-ribofuranosyl chloride that has been dissolved in 20 ml. ethylene dichloride is injected. This reaction mixture is stirred at the minus (−) 25° C. for 5 minutes before transferring the reaction vessel to a hot water bath where the reaction mixture is warmed to 20° C. Stirring is continued at the 20° C. temperature for 35 minutes when 100 ml. of saturated aqueous sodium bicarbonate is added. There is then added enough chloroform to bring the total volume to 400 ml. The organic phase is recovered and washed once with saturated aqueous sodium bicarbonate and once with water. It is dried by adding anhydrous magnesium sulfate. The dried organic solution is filtered to remove the magnesium sulfate and the filter is rinsed with 200 ml. chloroform. The chloroform is then removed by evaporation under reduced pressure to give 10.0 gm. of a foam. The foam is dissolved in 30 ml. chloroform and the solution is chromatographed over a series of three prepacked silica gel columns (E. Merck, 10609 Silica gel 60 per-packed column for liquid chromatography, size C). The columns are developed with a mixture of cyclohexane and acetone in proportions 2.5 to 1. The flow rate is 2 ml./min. and 20 ml. fractions are collected. The eluate in fractions 135 through 180 is recovered by combining the fractions and removing the solvents by evaporation. The product weighs 3.15 gm. An analytical sample is obtained by recrystallization from a mixture of acetone and Skellysolve B®(1:1 v/v). The product, 1-(3,5-di-O-toluoyl-2-deoxy-$\beta$-D-ribofuranosyl)-5-ethyl-5,6-dihydro-s-triazine-2,4-(1H,3H)-dione, has a melting point of 166.5° C. to 168° C.

Analysis: Calc'd for $C_{26}H_{29}N_3O_4$: C, 63.02; H, 5.90; N, 8.48. Found: C, 62.89; H, 5.88; N, 8.24.

$[\alpha]_D^{25} = -47°$ (c=0.885 in chloroform).

The eluate in fractions 191 through 246 is similarly recovered by combining the fractions and removing the solvents by evaporation. The product weighs 2.60 gm. An analytical sample is prepared by recrystallization from a mixture of acetone and Skellysolve B®(1:1 v/v). There is thus obtained pure 1-(3,5-di-O-toluoyl-2-deoxy-$\alpha$-D-ribofuranosyl)-5-ethyl-5,6-dihydro-s-triazine-2,4-(1H,3H)-dione having a melting point of 134.5° C. to 136° C.

Analysis: Calc'd for $C_{26}H_{29}N_3O_4$: C, 63.02; H, 5.90; N, 8.48. Found: C, 63.29; H, 5.93; N, 8.37.

$[\alpha]_D^{25} = 0°$ (c=0.8935 in chloroform).

Part C Preparation of compound 1-(2-deoxy-$\beta$-D-ribofuranosyl)-5-ethyl-5,6-dihydro-s-triazine-2,4-(1H,3H)-dione.

A reaction mixture is obtained by adding 0.33 ml. of a 25% solution of sodium methoxide in methanol to a solution consisting of 3.2 gm. (0.065 mole) of 1-(3,5-di-O-toluoyl-2-deoxy-$\beta$-D-ribofuranosyl)-5-ethyl-5,6-dihydro-s-triazine-2,4-(1H,3H)-dione (prepared in Part A, above) and 65 ml. methanol. The mixture was stirred for 18 hours. A few chips of solid carbon dioxide are added and the methanol is removed by evaporation under reduced pressure. The residue thus obtained is dispersed in a mixture of chloroform and water (20 ml. and 100 ml., respectively) and the aqueous phase is allowed to separate and is recovered. It is washed with four-20 ml. portions of chloroform and filtered. The water is removed from filtrate by evaporation under reduced pressure. The solid thus obtained is recrystallized from absolute ethanol to give 1.11 gm. of 1-(2-deoxy-$\beta$-D-ribofuranosyl)-5-ethyl-5,6-dihydro-s-triazine-2,4-(1H,3H)-dione having a melting point of 161.5° to 162.5° C.

Analysis: Calc'd for $C_{10}H_{17}N_3O_5$: C, 46.32; H, 6.61; N, 16.21. Found: C, 46.43; H, 6.74; N, 15.68.

$[\beta]_D^{25} = -7°$ (c=0.987 in water)

$NMR_{D_2O}$ gave $H_1'$, 3 line pattern at 6.19 $\delta$, and ring $CH_2$, 4.72 $\delta$, singlet.

Preparation 7 Preparation of 1-(2-deoxy-$\beta$-D-ribofuranosyl)-5,6-dihydro-5-methyl-s-triazine-2,4-(1H,3H)-dione and 3',5'-di-O-toluate thereof.

Part A Activated precursor 2,4-bis(trimethylsilyloxy)-5,6-dihydro-5-methyl-s-triazine.

A reaction mixture consisting of 1.3 gm. (0.010 mole) 5,6-dihydro-5-methyl-s-triazine-2,4-(1H,3H)-dione in 25 ml. pyridine and 6 ml. of bis-trimethylsilyltrifluoroacetamide containing 1% trimethylsilyl chloride is warmed to 50° C. and stirred for 16 hours. The mixture is then cooled to 25° C., and the pyridine medium along with other volatile components are removed by evaporation under reduced pressure at 60° C. The residue thus obtained is purified by distilling added toluene under reduced pressure. The toluene distillation is repeated, and any traces of toluene are removed by holding the residue under reduced pressure for 16 hours at 25° C. There is thus obtained a quantity (about 80% yield) of 2,4-bis-(trimethylsilyloxy)-5,6-dihydro-5-methyl-s-triazine.

Part B Alternative preparation of activated precursor 2,4-bis-(trimethylsilyloxy)-5,6-dihydro-5-methyl-s-triazine.

A reaction mixture consisting of 1.9 gm. (0.015 mole) of 5,6-dihydro-5-methyl-s-triazine-2,4-(1H,3H)-dione, 50 ml. hexamethyldisilazane, and 2 mg. ammonium sulfate is heated at the reflux temperature in an environment free from moisture for 48 hours. The mixture is then cooled to 25° C. and the excess hexamethyldisilazane is removed by evaporation under reduced pressure. The toluene is added to the residue thus obtained and anhydrous conditions are maintained by flushing with nitrogen gas. Toluene is removed by distillation. This toluene distillation is repeated; and the 2,4-bis(-trimethylsilyloxy)-5,6-dihydro-5-methyl-s-triazine thus obtained is kept under high vacuum until used.

Part C Synthesis of activated precursor 2-(trimethylsilyloxy)-5,6-dihydro-5-methyl-s-triazine-4-(3H)-one.

A reaction mixture consisting of 1.28 gm. (0.010 mole) 5,6-dihydro-5-methyl-s-triazine-2,4-(1H,3H)-dione, 40 ml. pyridine, and 4.0 ml. bis-trimethylsilyltrifluoroacetamide is stirred continuously at 25° C. for 18 hours. The volatiles are then removed by evaporation under reduced pressure, and the residue thus obtained is freed of any pyridine by adding acetonitrile and distilling under reduced pressure. The distillation is repeated and there is thus obtained a quantitative yield of 2-(trimethylsilyloxy)-5,6-dihydro-5-methyl-s-triazine-4-(3H)-one.

Part D Preparation of intermediate 1-(2-deoxy-3,5-di-O-toluoyl-$\beta$-D-ribofuranosyl)-5,6-dihydro-5-methyl-s-triazine-2,4-(1H,3H)-dione.

A solution consisting of 13.6 gm. (0.05 mole) of the activated precursor 2,4-bis(trimethylsilyloxy)-5,6-dihydro-5-methyl-s-triazine prepared in Part A, above, and 625 ml. acetonitrile is chilled to minus (−) 24° C. and 3.75 ml. of fuming anhydrous stannic chloride is added. This solution is stirred for five (5) minutes, in order to effect solution of the catalyst, before a room temperature (28° C.) solution consisting of 9.7 gm. (0.025 mole) of 2-deoxy-3,5-ditoluoyl-$\beta$-D-ribofuranosyl chloride and 100 ml. ethylene dichloride is added. This reaction mixture is stirred at minus (−) 20° C. for five (5) minutes before being warmed to 25° C. Stirring is continued as the solution gradually becomes a dark green color (when the reaction is considered complete). After adding 100 ml. of saturated aqueous sodium bicarbonate, the mixture is stirred for one (1) hour, and chloroform is added until an aqueous phase begins to separate. The aqueous phase is allowed to separate, and the organic phase is recovered. The organic phase is washed once with saturated aqueous sodium bicarbonate and once with water. All traces of moisture are removed by drying over anhydrous magnesium sulfate. The dried solution is filtered, and the magnesium sulfate on the filter is washed well with chloroform. The filtrate and washings are combined and the organic solvents are removed by evaporation under reduced pressure followed by high vacuum. The foamy residue is dissolved in 50 ml. ethyl acetate, and after seeding is set aside at 5° C. for 48 hours. The crystallizing mixture is shaken vigorously periodically during the 48 hours. The crystals are collected on a filter, washed well with ethyl acetate, and dried overnight under reduced pressure. There is thus obtained 3.46 gm. (28.8% yield) of the desired product. A pure sample is prepared by dissolving 2.0 gm. in 45 ml. hot ethyl acetate, filtering, concentrating the filtrate to one-third (⅓) its original volume, and crystallizing finally at minus (−) 20° C. There is thus obtained 1.6 gm. (80% yield) of 1-(2-deoxy-3,5-di-O-toluoyl-α-D-ribofuranosyl)-5,6-dihydro-5-methyl-s-triazine-2,4-(1H,3H)-dione having a melting point of 184° C. to 185° C.

Analysis: Calc'd for $C_{25}H_{27}N_3O_9$: C, 62.36; H, 5.65; N, 8.73. Found: C, 62.18; H, 5.69; N, 8.68.

U.V. λ end absorption, 241, 269, 281 nm (ε=31,800, 2,250, 1,300) ethanol

I.R. NH: 3200 $cm^{-1}$; NH/CH: 3080; C=O: 1730, 1710; C=C/βNH: 1610, 1575, 1520; C-C/C-N: 1275, 1265, 1250, 1180, 1110, 1100; other 755.

$[\alpha]_D$ −46° (c=1.087 in chloroform)

NMR: $J_1'-2'\alpha$=9 Hz. $J_1'-2'p$=6 Hz.

Part E Preparation of 1-(2-deoxy-3,5-di-O-toluoyl-(β-D-ribofuranosyl)-5,6-dihydro-5-methyl-s-triazine-2,4-(1H,3H)-dione from mono-silyloxy precursor, 2-(trimethylsilyloxy)-5,6-dihydro-5-methyl-s-triazine-4-(3H)-one.

Following the procedure described in Part C, above, but doubling the amounts of reactants and reagents and substituting the 2-(trimethylsilyloxy)-5,6-dihydro-5-methyl-s-triazine-4-(3H)-one for 2,4-bis(trimethylsilyloxy)-5,6-dihydro-5-methyl-s-triazine there is prepared the corresponding desired intermediate 1-(2-deoxy-3,5-di-O-toluoyl-β-D-ribofuranosyl)-5,6-dihydro-5-methyl-s-triazine-2,4-(1H,3H)-dione weighing 3.8 gm. and having a melting point of 183° C. to 185° C.

Part F Deacylation to obtain 1-(2-deoxy-β-D-ribofuranosyl)-5,6-dihydro-5-methyl-s-triazine-2,4-(1H,3H)-dione.

To a solution consisting of 7.85 gm. (0.016 mole) of 1-(2-deoxy-3,5di-O-toluoyl-β-D-ribofuranosyl)-5,6-dihydro-5-methyl-s-triazine-2,4-(1H,3H)-dione (prepared in Parts C and D, above) and 160 ml. methanol, is added 0.8 ml. of a 25% solution of sodium methoxide in methanol. This reaction mixture is stirred for 18 hours when a few chips of solid carbon dioxide are added and stirring is continued for another 10 minutes. Forty gm. of silica gel are added and the methanol is recovered by evaporation under reduced pressure. The residual white powder thus obtained is transferred to a column of silica gel and then the column is developed with a solution of 5% methanol in chloroform and fractions having positive U.V. absorption are combined. After removing the solvents by evaporation, a 1 gm. sample of the solid residue is dissolved in 4 ml. of hot methanol to which solution is added 24 ml. ethyl acetate. Crystallization occurs at 25° C., and there is thus obtained 0.79 gm. (79% recovery) of the compound having a melting point at 142° to 143° C.

Analysis: Calc'd for $C_9H_{15}N_3O_5$: c, 44.08; H, 6.17; N, 17.13. Found: c, 43.88; H, 6.18; N, 17.31.

Specific Rotation $[\alpha]_D^{25}$= −6° (c =0.9168, water)

Preparation 8

Part A

Following the procedure in Preparation 6, Part A, but substituting for the 5-ethyl-5,6-dihydro-s-triazine-2,4-(1H,3H)-dione,
3,4,5,6-tetrahydro-4-imino-s-triazine-2-(1H)-one,
3,4,5,6-tetrahydro-4-imino-5-methyl-s-triazine-2-(1H)-one,
3,4,5,6-tetrahydro-4-imino-5-ethyl-s-triazine-2-(1H)-one,
3,4,5,6-tetrahydro-4-imino-5-n-propyl-s-triazine-2-(1H)-one,
3,4,5,6-tetrahydro-4-imino-5-cyclopropyl-s-triazine-2-(1H)-one,
3,4,5,6-tetrahydro-4-imino-5-isopropyl-s-triazine-2-(1H)-one,
4-(acetylimino)-3,4,5,6-tetrahydro-s-triazine-2-(1H)-one,
4-(acetylimino)-3,4,5,6-tetrahydro-5-methyl-s-triazine-2-(1H)-one,
4-(acetylimino)-3,4,5,6-tetrahydro-5-ethyl-s-triazine-2-(1H)-one,
4-(acetylimino)-3,4,5,6-tetrahydro-5-n-propyl-s-triazine-2-(1H)-one,
4-(acetylimino)-3,4,5,6-tetrahydro-5-cyclopropyl-s-triazine-2-(1H)-one,
4-(acetylimino)-3,4,5,6-tetrahydro-5-isopropyl-s-triazine-2-(1H)-one,
5,6-dihydro-s-triazine-2,4-(1H,3H)-done,
6-methyl-5,6-dihydro-s-triazine-2,4-(1H,3H)-dione,
5-cyclopropyl-5,6-dihydro-s-triazine-2,4-(1H,3H)-dione,
5-n-propyl-5,6-dihydro-s-triazine-2,4-(1H,3H)-dione,
5-isopropyl-5,6-dihydro-s-triazine-2,4-(1H,3H)-dione,
5-methoxymethyl-5,6-dihydro-s-triazine-2,4-(1H,3H)-dione,
5-methylthiomethyl-5,6-dihydro-s-triazine-2,4-(1H,3H)-dione,
5-methyl-5,6-dihydro-2-thio-s-triazine-4-(1H,3H)-one,
5-ethyl-5,6-dihydro-2-thio-s-triazine-4-(1H,3H)-one,
there are prepared the corresponding:
3,4,5,6-tetrahydro-4-imino-2-O-trimethylsilyl-s-triazine,
3,4,5,6-tetrahydro-4-imino-5-methyl-2-O-trimethylsilyl-s-triazine,
3,4,5,6-tetrahydro-4-imino-5-ethyl-2-O-trimethylsilyl-s-triazine,
3,4,5,6-tetrahydro-4-imino-5-n-propyl-2-O-trimethylsilyl-s-triazine,
3,4,5,6-tetrahydro-4-imino-5-cyclopropyl-2-O-trimethyl-silyl-s-triazine,
3,4,5,6-tetrahydro-4-imino-5-isopropyl-2-O-trimethylsilyl-s-triazine,
4-(acetylimino)-3,4,5,6-tetrahydro-2-O-trimethylsilyl-s-triazine,
4-(acetylimino)-3,4,5,6-tetrahydro-5-methyl-2-O-trimethylsilyl-s-triazine,
4-(acetylimino)-3,4,5,6-tetrahydro-5-ethyl-2-O-trimethylsilyl-s-triazine,
4-(acetylimino)-3,4,5,6-tetrahydro-5-n-propyl-2-O-trimethylsilyl-s-triazine,
4-(acetylimino)-3,4,5,6-tetrahydro-5-cyclopropyl-2-O-trimethylsilyl-s-triazine,
4-(acetylimino)-3,4,5,6-tetrahydro-5-isopropyl-2-O-trimethylsilyl-s-triazine,
5,6-dihydro-2-O-trimethylsilyl-s-triazine-4-(3H)-one,
5,6-dihydro-6-methyl-2-O-trimethylsilyl-s-triazine-4-(3H)-one,
5,6-dihydro-5-cyclopropyl-2-O-trimethylsilyl-s-triazine-4-(3H)-one,
5,6-dihydro-5-n-propyl-2-O-trimethylsilyl-s-triazine-4-(3H)-one,
5,6-dihydro-5-isopropyl-2-O-trimethylsilyl-s-triazine-4-(3H)-one,
5,6-dihydro-5-methoxymethyl-2-O-trimethylsilyl-s-triazine-4-(3H)-one, 5,6-dihydro-5-methylthiomethyl-2-O-trimethylsilyl-s-triazine-4-(3H)-one,
5,6-dihydro-5-methyl-2-thio-trimethylsilyl-s-triazine-4-(3H)-one, and
5,6-dihydro-5-ethyl-2-thio-trimethylsilyl-s-triazine-4-(3H)-one, respectively.

Part B

Following the procedure described in Preparation 6, Part B, but substituting
3,4,5,6-tetrahydro-4-imino-2-O-trimethylsilyl-s-triazine,
3,4,5,6-tetrahydro-4-imino-5-methyl-2-O-trimethylsilyl-s-triazine,
3,4,5,6-tetrahydro-4-imino-5-ethyl-2-O-trimethylsilyl-s-triazine,
3,4,5,6-tetrahydro-4-imino-5-n-propyl-2-O-trimethylsilyl-s-triazine,
3,4,5,6-tetrahydro-4-imino-5-cyclopropyl-2-O-trimethyl-silyl-s-triazine,
3,4,5,6-tetrahydro-4-imino-5-isopropyl-2-O-trimethylsilyl-s-triazine,
4-(acetylimino)-3,4,5,6-tetrahydro-2-O-trimethylsilyl-s-triazine,
4-(acetylimino)-3,4,5,6-tetrahydro-5-methyl-2-O-trimethylsilyl-s-triazine,
4-(acetylimino)-3,4,5,6-tetrahydro-5-ethyl-2-O-trimethylsilyl-s-triazine,
4-(acetylimino)-3,4,5,6-tetrahydro-5-n-propyl-2-O-trimethylsilyl-s-triazine,
4-(acetylimino)-3,4,5,6-tetrahydro-5-cyclopropyl-2-O-trimethylsilyl-s-triazine,
4-(acetylimino)-3,4,5,6-tetrahydro-5-isopropyl-2-O-trimethylsilyl-s-triazine,
5,6-dihydro-2-O-trimethylsilyl-s-triazine-4-(3H)-one,
5,6-dihydro-6-methyl-2-O-trimethylsilyl-s-triazine-4-(3H)-one,
5,6-dihydro-5-cyclopropyl-2-O-trimethylsilyl-s-triazine-4-(3H)-one,
5,6-dihydro-5-n-propyl-2-O-trimethylsilyl-s-triazine-4-(3H)-one,
5,6-dihydro-5-isopropyl-2-O-trimethylsilyl-s-triazine-4-(3H)-one,
5,6-dihydro-5-methoxymethyl-2-O-trimethylsilyl-s-triazine-4-(3H)-one,
5,6-dihydro-5-methylthiomethyl-2-O-trimethylsilyl-s-triazine-4-(3H)-one,
5,6-dihydro-5-methyl-2-thio-trimethylsilyl-s-triazine-4-(3H)-one, and
5,6-dihydro-5-ethyl-2-thio-trimethylsilyl-s-triazine-4-(3H)-one respectively, for the 5-ethyl-5,6-dihydro-2-O-(trimethylsilyl)-s-triazine-4-(3H)-one, there are prepared the corresponding:
1-(2-deoxy-3,5-di-O-toluoyl-β-D-ribofuranosyl)-4-imino-3,4,5,6-tetrahydro-s-triazine-2-(1H)-one,
1-(2-deoxy-3,5-di-O-toluoyl-β-D-ribofuranosyl)-4-imino-3,4,5,6-tetrahydro-5-methyl-s-triazine-2-(1H)-one,
1-(2-deoxy-3,5-di-O-toluoyl-β-D-ribofuranosyl)-4-imino-3,4,5,6-tetrahydro-5-ethyl-s-triazine-2-(1H)-one,
1-(2-deoxy-3,5-di-O-toluoyl-β-D-ribofuranosyl)-4-imino-3,4,5,6-tetrahydro-5-propyl-s-triazine-2-(1H)-one,
1-(2-deoxy-3,5-di-O-toluoyl-β-D-ribofuranosyl)-4-imino-3,4,5,6-tetrahydro-5-cyclopropyl-s-triazine-2-(1H)-one,
1-(2-deoxy-3,5-di-O-toluoyl-β-D-ribofuranosyl)-4-imino-3,4,5,6-tetrahydro-5-isopropyl-s-triazine-2-(1H)-one,
1-(2-deoxy-3,5-di-O-toluoyl-β-D-ribofuranosyl)-4-(acetylimino)-3,4,5,6-tetrahydro-s-triazine-2-(1H)-one,
1-(2-deoxy-3,5-di-O-toluoyl-β-D-ribofuranosyl)-4-(acetylimino)-3,4,5,6-tetrahydro-5-methyl-s-triazine-2-(1H)-one,
1-(2-deoxy-3,5-di-O-toluoyl-β-D-ribofuranosyl)-4-(acetylimino)-3,4,5,6-tetrahydro-5-ethyl-s-triazine-2-(1H)-one,
1-(2-deoxy-3,5-di-O-toluoyl-β-D-ribofuranosyl)-4-(acetylimino)-3,4,5,6-tetrahydro-5-n-propyl-s-triazine-2-(1H)-one,
1-(2-deoxy-3,5-di-O-toluoyl-β-D-ribofuranosyl)-4-(acetylimino)-3,4,5,6-tetrahydro-5-cyclopropyl-s-triazine-2-(1H)-one,
1-(2-deoxy-3,5-di-O-toluoyl-β-D-ribofuranosyl)-4-(acetylimino)-3,4,5,6-tetrahydro-5-isopropyl-s-triazine-2-(1H)-one,
1-(2-deoxy-3,5-di-O-toluoyl-β-D-ribofuranosyl)-5,6-dihydro-s-triazine-2,4-(1H,3H)-dione,
1-(2-deoxy-3,5-di-O-toluoyl-β-D-ribofuranosyl)-5,6-dihydro-6-methyl-s-triazine-2,4-(1H,3H)-dione,
1-(2-deoxy-3,5-di-O-toluoyl-β-D-ribofuranosyl)-5,6-dihydro-5-cyclopropyl-s-triazine-2,4-(1H,3H)-dione,
1-(2-deoxy-3,5-di-O-toluoyl-β-D-ribofuranosyl)-5,6-dihydro-5-n-propyl-s-triazine-2,4-(1H,3H)-dione,
1-(2-deoxy-3,5-di-O-toluoyl-β-D-ribofuranosyl)-5,6-dihydro-5-isopropyl-s-triazine-2,4-(1H,3H)-dione,
1-(2-deoxy-3,5-di-O-toluoyl-β-D-ribofuranosyl)-5,6-dihydro-5-methoxymethyl-s-triazine-2,4-(1H,3H)-dione,
1-(2-deoxy-3,5-di-O-toluoyl-β-D-ribofuranosyl)-5,6-dihydro-5-methylthiomethyl-s-triazine-2,4-(1H,3H)-dione,
1-(2-deoxy-3,5-di-O-toluoyl-β-D-ribofuranosyl)-5,6-dihydro-5-methyl-2-thio-s-triazine-4-(1H,3H)-one, and
1-(2-deoxy-3,5-di-O-toluoyl-β-D-ribofuranosyl)-5,6-dihydro-5-ethyl-2-thio-s-triazine-4-(1H,3H)-one, respectively.

Part C

Following the procedure described in Preparation 6, Part C, but substituting.
1-(2-deoxy-3,5-di-O-toluoyl-β-D-ribofuranosyl)-4-imino-3,4,5,6-tetrahydro-s-triazine-2-(1H)-one,
1-(2-deoxy-3,5-di-O-toluoyl-β-D-ribofuranosyl)-4-imino-3,4,5,6-tetrahydro-5-methyl-s-triazine-2-(1H)-one,
1-(2-deoxy-3,5-di-O-toluoyl-β-D-ribofuranosyl)-4-imino-3,4,5,6-tetrahydro-5-ethyl-s-triazine-2-(1H)-one,
1-(2-deoxy-3,5-di-O-toluoyl-β-D-ribofuranosyl)-4-imino-3,4,5,6-tetrahydro-5-n-propyl-s-triazine-2-(1H)-one,
1-(2-deoxy-3,5-di-O-toluoyl-β-D-ribofuranosyl)-4-imino-3,4,5,6-tetrahydro-5-cyclopropyl-s-triazine-2-(1H)-one,
1-(2-deoxy-3,5-di-O-toluoyl-β-D-ribofuranosyl)-4-imino-3,4,5,6-tetrahydro-5-isopropyl-s-triazine-2-(1H)-one,
1-(2-deoxy-3,5-di-O-toluoyl-β-D-ribofuranosyl)-4-(acetylimino)-3,4,5,6-tetrahydro-s-triazine-2-(1H)-one,
1-(2-deoxy-3,5-di-O-toluoyl-β-D-ribofuranosyl)-4-(acetylimino)-3,4,5,6-tetrahydro-5-methyl-s-triazine-2-(1H)-one, 1-(2-deoxy-3,5-di-O-toluoyl-β-D-ribofuranosyl)-4-(acetylimino)-3,4,5,6-tetrahydro-5-ethyl-s-triazine-2-(1H)-one, 1-(2-deoxy-3,5-di-O-toluoyl-β-D-ribofuranosyl)-4-(acetylimino)-3,4,5,6-tetrahydro-5-n-propyl-s-triazine-2-(1H)-one, 1-(2-deoxy-3,5-di-O-toluoyl-β-D-ribofuranosyl)-4-(acetylimino)-3,4,5,6-tetrahydro-5-cyclopropyl-s-triazine-2-(1H)-one, 1-(2-deoxy-3,5-di-O-toluoyl-β-D-ribofuranosyl)-4-(acetylimino)-3,4,5,6-tetrahydro-5-isopropyl-s-triazine-2-(1H)-one, 1-(2-deoxy-3,5-di-O-toluoyl-β-D-ribofuranosyl)-5,6-dihydro-s-triazine-2,4-(1H,3H)-dione, 1-(2-deoxy-3,5-di-O-toluoyl-β-D-ribofuranosyl)-5,6-dihydro-6-methyl-s-triazine-2,4-(1H,3H)-dione, 1-(2-deoxy-3,5-di-O-toluoyl-β-D-ribofuranosyl)-5,6-dihydro-5-cyclopropyl-s-triazine-2,4-(1H,3H)-dione, 1-(2-deoxy-3,5-di-O-toluoyl-β-D-ribofuranosyl)-5,6-dihydro-5-n-propyl-s-triazine-2,4-(1H,3H)-dione, 1-(2-deoxy-3,5-di-O-toluoyl-β-D-ribofuranosyl)-5,6-dihydro-5-isopropyl-s-triazine-2,4-(1H,3H)-dione, 1-(2-deoxy-3,5-di-O-toluoyl-β-D-ribofuranosyl)-5,6-dihydro-5-methoxymethyl-s-triazine-2,4-(1H,3H)-dione, 1-(2-deoxy-3,5-di-O-toluoyl-β-D-ribofuranosyl)-5,6-dihydro-5-methylthiomethyl-s-triazine-2,4-(1H,3H)-dione, 1-(2-deoxy-3,5-di-O-toluoyl-β-D-ribofuranosyl)-5,6-dihydro-5-methyl-2-thio-s-triazine-4-(1H,3H)-one, and 1-(2-deoxy-3,5-di-O-toluoyl-β-D-ribofuranosyl)-5,6-dihydro-5-ethyl-2-thio-s-triazine-4-(1H,3H)-one, for the 1-(2-deoxy-3,5-di-O-toluoyl-β-D-ribofuranosyl)-5-ethyl-5,6-dihydro-s-triazine-2,4-(1H,3H)-dione, there are prepared the corresponding:

1-(2-deoxy-β-D-ribofuranosyl)-4-imino-3,4,5,6-tetrahydro-s-triazine-2-(1H)-one, 1-(2-deoxy-β-D-ribofuranosyl)-4-imino-5-methyl-3,4,5,6-tetrahydro-s-triazine-2-(1H)-one, 1-(2-deoxy-β-D-ribofuranosyl)-4-imino-5-ethyl-3,4,5,6-tetrahydro-s-triazine-2-(1H)-one, 1-(2-deoxy-β-D-ribofuranosyl)-4-imino-5-n-propyl-3,4,5,6-tetrahydro-s-triazine-2-(1H)-one, 1-(2-deoxy-β-D-ribofuranosyl)-4-imino-5-cyclopropyl-3,4,5,6-tetrahydro-s-triazine-2-(1H)-one, 1-(2-deoxy-β-D-ribofuranosyl)-4-imino-5-isopropyl-3,4,5,6-tetrahydro-s-triazine-2-(1H)-one, 1-(2-deoxy-β-D-ribofuranosyl)-5,6-dihydro-s-triazine-2,4-(1H,3H)-dione, 1-(2-deoxy-β-D-ribofuranosyl)-5,6-dihydro-6-methyl-s-triazine-2,4-(1H,3H)-dione, 1-(2-deoxy-β-D-ribofuranosyl)-5,6-dihydro-5-cyclopropyl-s-triazine-2,4-(1H,3H)-dione, 1-(2-deoxy-β-D-ribofuranosyl)-5,6-dihydro-5-n-propyl-s-triazine-2,4-(1H,3H)-dione, 1-(2-deoxy-β-D-ribofuranosyl)-5,6-dihydro-5-isopropyl-s-triazine-2,4-(1H,3H)-dione, 1-(2-deoxy-β-D-ribofuranosyl)-5,6-dihydro-5-methoxymethyl-s-triazine-2,4-(1H,3H)-dione, 1-(2-deoxy-β-D-ribofuranosyl)-5,6-dihydro-5-methylthio-s-triazine-2,4-(1H,3H)-dione, 1-(2-deoxy-β-D-ribofuranosyl)-5,6-dihydro-5-methyl-2-thio-s-triazine-4-(1H,3H)-one, and 1-(2-deoxy-β-D-ribofuranosyl)-5,6-dihydro-5-ethyl-2-thio-s-triazine-4-(1H,3H)-one.

Preparation 9

Following the procedure described in Preparation 6, Part B, but substituting 1-(2-deoxy-3,5-di-O-acetyl-D-ribofuranosyl)-chloride,
1-(2-deoxy-3,5-di-O-toluoyl-D-ribofuranosyl)-bromide,
1-(2-deoxy-3,5-di-O-benzoyl-D-ribofuranosyl)-chloride,
1-(2-deoxy-3,5-di-O-p-nitrobenzoyl-D-ribofuranosyl)-chloride,
1-(2-deoxy-3,5-di-O-p-chlorobenzoyl-D-ribofuranosyl)-chloride,
1-(2-deoxy-3,5-di-O-toluoyl-D-xylofuranosyl)-chloride for the 1-(2-deoxy-3,5-di-O-toluoyl-D-ribofuranosyl)-chloride, there are prepared the corresponding:

1-(2-deoxy-3,5-di-O-acetyl-β-D-ribofuranosyl)-5-ethyl-5,6-dihydro-s-triazine-2,4-(1H,3H)-dione, 1-(2-deoxy-3,5-di-O-toluoyl-β-D-ribofuranosyl)-5-ethyl-5,6-dihydro-s-triazine-2,4-(1H,3H)-dione, 1-(2-deoxy-3,5-di-O-benzoyl-β-D-ribofuranosyl)-5-ethyl-5,6-dihydro-s-triazine-2,4-(1H,3H)-dione, and 1-(2-deoxy-3,5-di-O-p-nitrobenzoyl-β-D-ribofuranosyl)-5-ethyl-5,6-dihydro-s-triazine-2,4-(1H,3H)-dione, and 1-(2-deoxy-3,5-di-O-p-chlorobenzoyl-β-D-ribofuranosyl)-5-ethyl-5,6-dihydro-s-triazine-2,4-(1H,3H)-dione, and 1-(2-deoxy-3,5-di-O-toluoyl-β-D-xylofuranosyl)-5-ethyl-5,6-dihydro-s-triazine-2,4-(1H,3H)-dione, respectively.

Preparation 10 Preparation of
1-(2-deoxy-3-O-lauroyl-β-D-ribofuranosyl)-5,6-dihydro-5-methyl-s-triazine-2,4-(1H,3H)-dione.

Part A  1-(5-tert-butyldimethylsilyl-2-deoxy-β-D-ribofuranosyl)-5-methyl-5,6-dihydro-s-triazine-2,4-(1H,3H)- dione.

A reaction mixture consisting of 12.25 gm. (0.050 mole) of 1-(2-deoxy-β-D-ribofuranosyl)-5,6-dihydro-5-methyl-s-triazine-2,4-(1H,3H)-dione, 50 ml. dimethylformamide, and 8.5 gm. (0.125 mole) of imidazole was warmed to 35° C. and stirred until the imidazole had dissolved. There was then added with continued stirring 7.55 gm. (0.050 mole) tert-butyldimethylsilyl chloride. Stirring was continued for 18 hours at 35° C. The solvent medium was then removed by evaporation under reduced pressure, and the residue thus obtained was dispersed in a solvent mixture consisting of 200 ml. chloroform and 50 ml. water. The two phases were allowed to stabilize and the aqueous phase was recovered. It was washed two times with 50 ml. portions of chloroform. The three chloroform layers (original and two washings) were combined and washed with three-25 ml. portions of water. The washed chloroform solution was dried over anhydrous magnesium sulfate and filtered. The chloroform was then removed by evaporation under reduced pressure to give 14.8 gm. (82.5% yield) of 1-(5-tert-butyldimethylsilyl-2-deoxy-β-D-ribofuranosyl)5,6-dihydro-5-methyl-s-triazine-2,4-(1H,3H)-dione.

Part B  1-(5-tert-butyldimethylsilyl-3-O-lauroyl-2-deoxy-β-D-ribofuranosyl)-5,6-dihydro-5-methyl-s-triazine-2,4-(1H,3H)-dione.

To a solution consisting of 3.59 gm. (0.010 mole) of 1-(5-tert-butyldimethylsilyl-2-deoxy-β-D-ribofuranosyl)-5-methyl-5,6-dihydro-s-triazine-2,4-(1H,3H)-dione and 30 ml. A. R. pyridine that had been cooled to 5° C. was added, with stirring, 2.55 gm.

(0.0116 mole) of freshly distilled lauroyl chloride. This reaction mixture was stirred for 18 hours at 25° C. Then it was cooled to 10° C. and 3 ml. water was added. This mixture was stirred at 25° C. while the solvents were removed by evaporation under reduced pressure. The residue thus obtained was dispersed in a solvent mixture consisting of 100 ml. chloroform and 50 ml. saturated aqueous sodium bicarbonate. The aqueous and organic phases were allowed to stabilize and the organic phase was saved. It was washed two times with 50 ml. portions of saturated aqueous sodium bicarbonate and dried over anhydrous magnesium sulfate. The dried chloroform solution was filtered and the filter was washed with chloroform. The filtrate and washings were combined and the chloroform was removed by evaporation under reduced pressure. There was thus obtained 4.8 gm. (88.7% yield) of 1-(5-tert-butyldimethylsilyl-3-O lauroyl-2-deoxy-β-D-ribofuranosyl)-5,6-dihydro-5-methyl-s-triazine-2,4-(1H,3H)-dione.

Following the same procedure, but substituting 1-(2-deoxy-β-D-ribofuranosyl)-5-ethyl-5,6-dihydro-s-triazine-2,4-(1H,3H)-dione,
1-(2-deoxy-β-D-ribofuranosyl)-5-n-propyl-5,6-dihydro-s-triazine-2,4-(1H,3H)-dione,
1-(2-deoxy-β-D-ribofuranosyl)-5-cyclopropyl-5,6-dihydro-s-triazine-2,4-(1H,3H)-dione, and
1-(2-deoxy-β-D-ribofuranosyl)-3,4,5,6-tetrahydro-4-imino-5-methyl-s-triazine-2-(1H)-one for the 1-(5-tert-butyldimethylsilyl-2-deoxy-β-D-ribofuranosyl)-5,6-dihydro-5-methyl-s-triazine-2,4-(1H,3H)-dione there are prepared the corresponding:
1-(2-deoxy-5-lauroyl-β-D-ribofuranosyl)-5-ethyl-5,6-dihydro-s-triazine-2,4-(1H,3H)-dione,
1-(2-deoxy-5-lauroyl-β-D-ribofuranosyl)-5,6-dihydro-5-n-propyl-s-triazine-2,4-(1H,3H)-dione,
1-(2-deoxy-5-lauroyl-β-D-ribofuranosyl)-5-cyclopropyl-5,6-dihydro-s-triazine-2,4-(1H,3H)-dione, and
1-(2-deoxy-5-lauroyl-β-D-ribofuranosyl)-4-imino-5-methyl-3,4,5,6-tetrahydro-s-triazine-2-(1H)-one, respectively, Part C 1-(2-Deoxy-3-lauroyl-β-D-ribofuranosyl)-5,6-dihydro-5-methyl-s-triazine-2,4-(1H,3H)-dione.

A reaction mixture consisting of 4.8 gm. (0.009 mole) of 2-(5-tert-butyldimethylsilyl-3-lauroyl-2-deoxy-β-D-ribofuranosyl)-5,6-dihydro-5-methyl-s-triazine-2,4-(1H,3H)-dione. 26 ml. tetrahydrofuranosyl, and 28 ml. tetra-n-butyl ammonium fluoride in tetrahydrofuran was allowed to stand for 18 hours at 25° C. The medium was then removed by evaporation under reduced pressure, and the residue thus obtained was dissolved in 200 ml. chloroform. The chloroform solution was washed with two-50 ml. portions of saturated aqueous sodium bicarbonate and three-50 ml. portions water, and then dried over anhydrous magnesium sulfate. The washed chloroform solution was filtered and the residue was washed with additional chloroform which was added to the filtrate. The chloroform was then removed by evaporation under reduced pressure to give a semi-solid residue. This residue was dissolved in 25 ml. acetone and technical hexane was added to the acetone solution until it became cloudy. After seeding, the cloudy solution was allowed to crystallize for 18 hours at 25° C. The crystals were collected on a filter and washed with a mixture of acetone and technical hexane. There was thus obtained 1.41 gm. of 1-(2-deoxy-3-lauroyl-β-D-ribofuranosyl)-5,6-dihydro-5-methyl-s-triazine-2,4-(1H,3H)-dione. An analytical sample was prepared by recrystallizing 1.4 gm. from a mixture of 20 ml. acetone and 25 ml. hexane. It weighed 1.15 gm. and had a melting point at 136° C. to 137° C.

Analysis: Calc'd for $C_{21}H_{37}N_3O_8$: C, 58.99; H, 8.72; N, 9.82. Found: C, 58.83; H, 8.98; N, 9.43.

IR: OH: 3480 cm$^{-1}$; NH: 3200, 3080; C=O: 1740, 1710, 1695, and 1685; βNH/other: 1520; C-O/C-N: 1270, 1165, 1105; Other: 725.

The following is a comparative test of 1-(2-deoxy-β-D-ribofuranosyl)-5-ethyl-5,6-dihydro-s-triazine-2,4-(1H,3H)-dione, U-50,365 and 1-(2-deoxy-β-D-ribofuranosyl)-5-methyl-5,6-dihydro-s-triazine-2,4-(1H,3H)-dione, U-44,590. Mean survial time (MST) in days and percent survivors (% S) is given. The compounds are administered subcutaneously to mice which are inoculated intravenously with $3\times10^5$ PFU (MRS) Herpes simplex virus (HSV-1). Treatment is initiated one hour after virus inoculation and is followed by treatment three times daily for five consecutive days. A detailed account of the materials, methods and results are as follows.

Male mice, weighing approximately 18 gm. each, are divided into eight groups of 20. Group 1 is treated with Sterile saline, group 2 with 400 mg./kg./dose (mkd) U-44,590, group 3 with 200 mkd U-44,590, group 4 with 100 mkd U-44,590, group 5 with 50 mkd U-44,590, group 6 with 200 mkd U-50,365, group 7 with 100 mkd U-50,365, and group 8 with 50 mkd U-50,365. The test compound is dissolved in Sterile saline and administered subcutaneously in the nape of the neck at 8:00 a.m., 12:00 noon, and 4:00 p.m. on days 1, 2, 3 and 4. $3\times10^5$ PFU (MRS) herpes simplex virus (HSV-1) is inoculated into the tail vein at 8:00 a.m. on day 0. On day 0, the test compound is given at 9:00 a.m. 12:00 noon, and 4:00 p.m. Death and paralysis are recorded daily.

Hind leg paralysis usually preceeded death by 1–2 days. All mice died that became paralyzed. Death pattern of the 8 groups, as shown in the curves of Table I illustrates the dose response obtained.

In addition to its antiviral activity, U-50,365 is less cytotoxic than U-44,590 and as determined by Standard microbiological disk plate assays did not exhibit antibacterial activity against *Bacillus subtilis, Staphylococcus aivieus, Sarcina lutea, Klebsiella pheumoniae, Escherichia coli, Salmonella schottmulleri, Proteus vulgaris, Mycobacterium avium, Penicillium oxalicum, Saccharomyces pastorianus Pseudomonas aeruqinosa* or *Pseudomonas fluorescens* with assay disks treated with 20 microliters of a 1 mg./ml. aqueous solution of U-50,365.

We claim:

1. A process for treating susceptible DNA viral infectious disease in a human and animal host without exhibiting anti-bacterial activity against *Escherichia coli* which comprises administering to the viral host an effective therapeutic amount for the treatment of susceptible DNA viral infections of a compound of the formula:

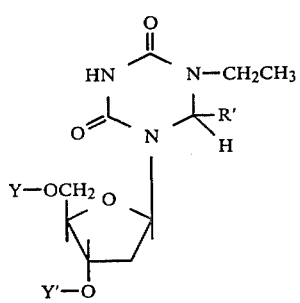

wherein R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen; and pharmaceutically acceptable salts thereof, in combination with a pharmaceutical carrier.

2. A process according to claim 1, wherein R' of the compound is hydrogen.

3. A process according to claim 1, wherein Y and Y' of the compound are hydrogen.

4. A process according to claim 1, wherein Y and Y' of the compound are carboxacyl of from 1 through 18 carbon atoms and R' is hydrogen.

5. A process according to claim 1, wherein Y of the compound is carboxacyl of from 1 through 18 carbon atoms, and Y' and R' are hydrogen.

6. A process according to claim 1, wherein Y' of the compound is carboxacyl of from 1 through 18 carbon atoms, and Y and R' are hydrogen.

7. A process according to claim 1, wherein the compound of the formula is administered to the infected host in unit dosage form in an amount of from about 300 mg/kg/day to about 3200 mg/kg/day of said compound in association with a pharmaceutical carrier.

8. A process according to claim 1, wherein the compound is 1-(2-deoxy-β-D-ribofuranosyl)-5-ethyl-5,6-dihydro-s-triazine-2,4-(1H,3H)-dione.

9. A process for treating susceptible herpes viral infectious disease in a human and animal host without exhibiting anti-bacterial activity against *Escherichia coli* which comprises administering to the viral host an effective therapeutic amount for the treatment of susceptible Herpes viral infections of a compound of the formula:

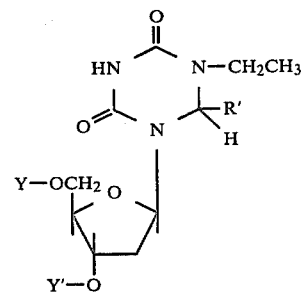

wherein R' is selected from the group consisting of hydrogen and lower alkyl of 1 through 4 carbon atoms; Y is selected from the group consisting of hydrogen, carboxacyl of from 1 through 18 carbon atoms, and phosphono; and Y' is selected from the group consisting of carboxacyl of from 1 through 18 carbon atoms and hydrogen; and pharmaceutically acceptable salts thereof, in combination with a pharmaceutical carrier.

10. A process according to claim 9, wherein R' of the compound is hydrogen.

11. A process according to claim 9, wherein Y and Y' of the compound are hydrogen.

12. A process according to claim 9, wherein Y and Y' of the compound are carboxacyl of from 1 through 18 carbon atoms and R' is hydrogen.

13. A process according to claim 9, wherein Y of the compound is carboxacyl of from 1 through 18 carbon atoms, and Y' and R' are hydrogen.

14. A process according to claim 9, wherein Y' of the compound is carboxacyl of from 1 through 18 carbon atoms, and Y and R' are hydrogen.

15. A process according to claim 9, wherein the compound of the formula is administered to the infected host in unit dosage form in an amount of from about 300 mg/kg/day to about 3200 mg/kg/day of said compound in association with a pharmaceutical carrier.

16. A process according to claim 9, wherein the compound is 1-(2-deoxy-β-D-ribofuranosyl)-5-ethyl-5,6-dihydro-s-triazine-2,4-(1H,3H)-dione.

17. A process for treating susceptible DNA viral infectious disease in a human and animal host without exhibiting anti-bacterial activity against *Escherichia coli* which comprises administering to the viral host an effective amount for the treatment of susceptible DNA viral infections of 1-(2-deoxy-β-D-ribofuranosyl)-5-ethyl-5,6-dihydro-s-triazine-2,4-(1H,3H)-dione.

18. A process for treating susceptible herpes viral infectious disease in a human and animal host without exhibiting anti-bacterial activity against *Escherichia coli* which comprises administering to the viral host an effective amount for the treatment of susceptible herpes viral infections of 1-(2-deoxy-β-D-ribofuranosyl)-5-ethyl-5,6-dihydro-s-triazine-2,4-(1H,3H)-dione.

* * * * *